United States Patent
Nishikawa et al.

(10) Patent No.: US 8,785,886 B2
(45) Date of Patent: Jul. 22, 2014

(54) OPTICAL ANALYSIS METHOD USING THE LIGHT INTENSITY OF A SINGLE LIGHT-EMITTING PARTICLE

(71) Applicant: Olympus Corporation, Tokyo (JP)

(72) Inventors: Kazutaka Nishikawa, Hachioji (JP); Tetsuya Tanabe, Tokyo (JP); Mitsushiro Yamaguchi, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/788,972

(22) Filed: Mar. 7, 2013

(65) Prior Publication Data

US 2013/0228705 A1    Sep. 5, 2013

Related U.S. Application Data

(63) Continuation of application No. PCT/JP2011/069738, filed on Aug. 31, 2011.

(30) Foreign Application Priority Data

Sep. 10, 2010  (JP) ................. 2010-202995

(51) Int. Cl.
*G01N 21/64* (2006.01)
*H01J 65/06* (2006.01)
*G01N 15/14* (2006.01)

(52) U.S. Cl.
CPC ........ *G01N 21/64* (2013.01); *G01N 2015/1493* (2013.01); *G01N 21/6452* (2013.01); *G01N 21/6428* (2013.01); *G01N 15/1463* (2013.01)
USPC .................. 250/461.2; 250/459.1; 250/458.1; 250/461.1

(58) Field of Classification Search
USPC .................. 250/461.2, 459.1, 458.1, 461.1
See application file for complete search history.

(56) References Cited

U.S. PATENT DOCUMENTS

| 4,251,733 A | 2/1981 | Hirleman, Jr. |
| 5,866,336 A | 2/1999 | Nazarenko et al. |

(Continued)

FOREIGN PATENT DOCUMENTS

| EP | 1 906 172 A1 | 4/2008 |
| JP | 4-337446 A | 11/1992 |

(Continued)

OTHER PUBLICATIONS

Masataka Kinjo, "Single molecule protein, nucleic acid, and enzyme assays and their procedures Single molecule detection by fluorescence correlation spectroscopy", Protein, Nucleic acid Enzyme vol. 44, No. 9, 1999, pp. 1431-1438. (cited in specification; w/English trans).

(Continued)

*Primary Examiner* — David Porta
*Assistant Examiner* — Kenneth J Malkowski
(74) *Attorney, Agent, or Firm* — Westerman, Hattori, Daniels & Adrian, LLP

(57) ABSTRACT

There is provided a scanning molecule counting method using an optical measurement with a confocal microscope or a multiphoton microscope, enabling characterization of a light-emitting particle or identification of a light-emitting particle with emitted light intensity of a single light-emitting particle measured individually. In the inventive optical analysis technique, with reference to the ratio of the intensities of simultaneously generated signals of the lights of at least two light-emitting sites having mutually different emission wavelengths, possessed by a light-emitting particle contained in a sample solution, the intensities being measured with moving the position of the light detection region of an optical system by changing the optical path of the optical system, a single light-emitting particle corresponding to the signals is identified, and the kind, the size, etc. of the light-emitting particle is identified.

10 Claims, 9 Drawing Sheets

(56) References Cited

U.S. PATENT DOCUMENTS

Figure 1A:
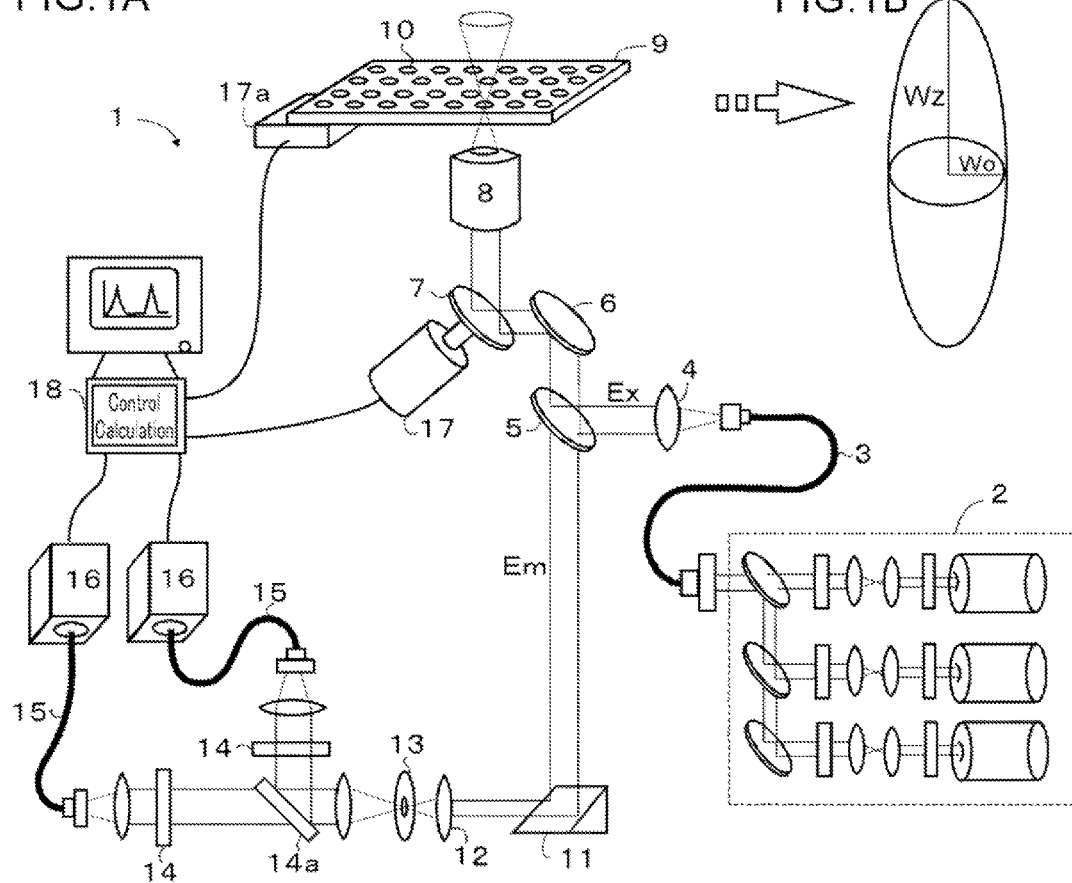

| | | |
|---|---|---|
| 6,280,960 B1 | 8/2001 | Carr |
| 6,376,843 B1 | 4/2002 | Palo |
| 6,388,746 B1 | 5/2002 | Eriksson et al. |
| 6,388,788 B1 | 5/2002 | Harris et al. |
| 6,400,487 B1 | 6/2002 | Harris et al. |
| 6,403,338 B1 | 6/2002 | Knapp et al. |
| 6,710,871 B1 | 3/2004 | Goix |
| 6,856,391 B2 | 2/2005 | Garab et al. |
| 6,927,401 B1 | 8/2005 | Palo |
| 8,284,484 B2 | 10/2012 | Hoult et al. |
| 8,471,220 B2 | 6/2013 | Yamaguchi et al. |
| 2001/0035954 A1 | 11/2001 | Rahn et al. |
| 2002/0008211 A1 | 1/2002 | Kask |
| 2002/0036775 A1 | 3/2002 | Wolleschensky et al. |
| 2003/0036855 A1 | 2/2003 | Harris et al. |
| 2003/0218746 A1* | 11/2003 | Sampas .................. 356/318 |
| 2004/0022684 A1 | 2/2004 | Heinze et al. |
| 2004/0051051 A1 | 3/2004 | Kato et al. |
| 2004/0150880 A1 | 8/2004 | Nakata et al. |
| 2004/0219535 A1 | 11/2004 | Bell et al. |
| 2005/0179892 A1 | 8/2005 | Gerstner et al. |
| 2005/0213090 A1* | 9/2005 | Namba et al. ............ 356/318 |
| 2005/0260660 A1 | 11/2005 | van Dongen et al. |
| 2006/0078998 A1 | 4/2006 | Puskas et al. |
| 2006/0158721 A1 | 7/2006 | Nakata et al. |
| 2006/0256338 A1 | 11/2006 | Gratton et al. |
| 2008/0052009 A1 | 2/2008 | Chiu et al. |
| 2008/0117421 A1 | 5/2008 | Yamaguchi et al. |
| 2009/0159812 A1 | 6/2009 | Livingston |
| 2009/0230324 A1 | 9/2009 | Gratton et al. |
| 2010/0033718 A1 | 2/2010 | Tanaami |
| 2010/0177190 A1 | 7/2010 | Chiang et al. |
| 2010/0202043 A1 | 8/2010 | Ujike |
| 2011/0204258 A1* | 8/2011 | Heller et al. ............ 250/459.1 |
| 2012/0029831 A1 | 2/2012 | Hoshishima et al. |
| 2012/0318956 A1 | 12/2012 | Yamaguchi et al. |

FOREIGN PATENT DOCUMENTS

| | | | |
|---|---|---|---|
| JP | 2002-022640 A | 1/2002 | |
| JP | 2002-507762 A | 3/2002 | |
| JP | 2002-525579 A | 8/2002 | |
| JP | 2002-543414 A | 12/2002 | |
| JP | 2003-522969 A | 7/2003 | |
| JP | 2004-506192 A | 2/2004 | |
| JP | 3517241 B2 | 4/2004 | |
| JP | 2004-251814 A | 9/2004 | |
| JP | 2005-98876 A | 4/2005 | |
| JP | 2005-99662 A | 4/2005 | |
| JP | 2005-509857 A | 4/2005 | |
| JP | 2005-524051 A | 8/2005 | |
| JP | 2006-525517 A | 11/2006 | |
| JP | 2007-20565 A | 2/2007 | |
| JP | 4023523 B2 | 12/2007 | |
| JP | 2008-116440 A | 5/2008 | |
| JP | 2008-536093 A | 9/2008 | |
| JP | 2008-538609 A | 10/2008 | |
| JP | 2008-292371 A | 12/2008 | |
| JP | 2009-145242 A | 7/2009 | |
| JP | 2009-281831 A | 12/2009 | |
| JP | 2009-288161 A | 12/2009 | |
| JP | 2010-190730 A | 9/2010 | |
| JP | 2011-002415 A | 1/2011 | |
| WO | 98/16814 A1 | 4/1998 | |
| WO | 99/47963 A | 9/1999 | |
| WO | 00/16101 A2 | 3/2000 | |
| WO | 00/66985 A1 | 11/2000 | |
| WO | 01/59432 A2 | 8/2001 | |
| WO | 02/12864 A1 | 2/2002 | |
| WO | 03/021212 A1 | 3/2003 | |
| WO | 03/042695 A1 | 5/2003 | |
| WO | 2004/099778 A1 | 11/2004 | |
| WO | 2006/084283 A2 | 8/2006 | |
| WO | 2006/115870 A2 | 11/2006 | |
| WO | 2007/010803 A1 | 1/2007 | |
| WO | 2007/147159 A2 | 12/2007 | |
| WO | 2008/007580 A1 | 1/2008 | |
| WO | 2008/080417 A1 | 7/2008 | |
| WO | 2009/117033 A2 | 9/2009 | |
| WO | 2010/084719 A1 | 7/2010 | |
| WO | 2011/108369 A1 | 9/2011 | |
| WO | 2011/108371 A1 | 9/2011 | |

OTHER PUBLICATIONS

F.J. Meyer-Almes, "A new Method for Use in Molecular Diagnostics and High Throughput Pharmaceutical Screening based on Fluorescence Correlation Spectroscopy", Nanoparticle Immunoassays, R. Rigler, edit, Springer, Berlin, 2000, pp. 204-224. (cited in specification).

Noriko Kato et al., "A single molecule analyzer that enable new analysis of DNA and protein interactions", Gene Medicine, vol. 6, No. 2, 2002, pp. 271-277. (cited in specification).

Peet Kask et al., "Fluorescence-intensity distribution analysis and its application in biomolecular detection technology", PNAS, vol. 96, No. 24, Nov. 23, 1999, pp. 13756-13761. (cited in specification).

International Search Report for PCT/JP2011/069738, mailing date of Dec. 13, 2011.

International Search Report of PCT/JP2011/053481, mailing date Mar. 29, 2011.

Park et al., "Counting the number of Fluorophores Labeled in Biomolecules by Observing the Fluorescence-Intensity Transient of a Single Molecule", Bulletin of the Chemical Society of Japan, vol. 78, No. 9, p. 1612-1618, Aug. 30, 2005.

U.S. Office Action mailed Apr. 2, 2013, issued in related U.S. Appl. No. 13/596,280.

P. Kask et al., "Two-Dimensional Fluorescence Intensity Distribution Analysis: Theory and Applications", Biophysical Journal, vol. 78, pp. 1703-1713, (2000), Cited in Specification.

Carlsson K et al: "Three-dimensional microscopy using a confocal laser scanning microscope", Optics Letters, Optical Society of America, vol. 10, No. 2, Feb. 1985 pp. 53-55, XP007922413.

Chinese Office Action dated Aug. 13, 2013, issued in related Chinese application No. 201180011655.3 with translation.

International Search Report dated Mar. 29, 2011, issued in related PCT/JP2011/053483.

International Preliminary Report on Patentability (PCT/IPEA/409) issued in related PCT/JP2011/053483.

Chinese Office Action dated Aug. 9, 2013, issued in related Chinese application No. 201180011640.7 with translation.

International Search Report issued in related PCT/JP2011/053482, mailing date Mar. 29, 2011.

International Preliminary Report on Patentability (PCT/IPEA/409) issued in related PCT/JP2011/053482.

U.S. Office Action dated Jan. 3, 2013, issued in related U.S. Appl. No. 13/597,825.

Chinese Office Action dated Feb. 7, 2013, issued in related Chinese application No. 201180011644.5 with translation.

Extended European search report dated Mar. 28, 2013, issued in related EP application No. 11750481.

Japan Office Action dated Dec. 18, 2012, issued in related JP application No. 2012-503060 with translation.

International Preliminary Report on Patentability (PCT/IPEA/409) issued in related PCT/JP2011/053481.

Goodwin et al. "Rapid sizing of individual fluorescently stained DNA fragments by flow cytometry," Nucleic Acids Research, 1993, vol. 21, No. 4 pp. 803-806.

Keller et al. "Single-Molecule Fluorescence Analysis in Solution," Applied Spectroscopy, 1996, vol. 50, No. 7, pp. 12A-32A.

Lee et al. "Laser-Induced Fluorescence Detection of a Single Molecule in a Capillary," Analytical Chemistry, Dec. 1, 1994, vol. 66, No. 23, pp. 4142-4149.

Li et al. "Ultrasensitive Coincidence Fluorescence Detection of Single DNA Molecule," Analytical Chemistry, Apr. 1, 2003, vol. 75, No. 7, pp. 1664-1670.

Nie et al. "Probing Individual Molecules with Confocal Fluorescence Microscopy," Science, Nov. 11, 1994, vol. 266, pp. 1018-1021.

(56) References Cited

OTHER PUBLICATIONS

Tahari, "Fluorescence Correlation Spectroscopy: Ultrasensitive Detection in Clear and Turbid Media," University of Illinois, 2005, pp. 1-88.

Wu et al. "Development and Preliminary Clinical Validation of a High Sensitivity Assay for Cardiac Troponin Using a Capillary Flow (Single Molecule) Fluorescence Detector," Clinical Chemistry, 2006, vol. 52, No. 11, pp. 2157-2159.

Itoh et al. "A New Method for Detection of Influenza Viruses by Single Particle-Recognition Based on the Principle of Fluorescence Correlation Spectroscopy," Chemistry and Biology, 2009, vol. 47, No. 12, pp. 823-830.

U.S. Office Action dated Oct. 4, 2013, issued in related U.S. Appl. No. 13/596,243.

Schwille, Petra, et al., "Dual-Color Fluorescence Cross-Correlation Spectroscopy for Multicomponent Diffusional Analysis in Solution", Biophysical Journal, 1997, vol. 72, pp. 1878-1886, cited in specification.

International Search Report of PCT/JP2011/069440, mailing date of Nov. 29, 2011.

International Search Report of PCT/JP2011/076151, mailing date of Feb. 14, 2012.

Extended European search report dated Dec. 20, 2013, issued in related EP application No. 11843762.3.

* cited by examiner

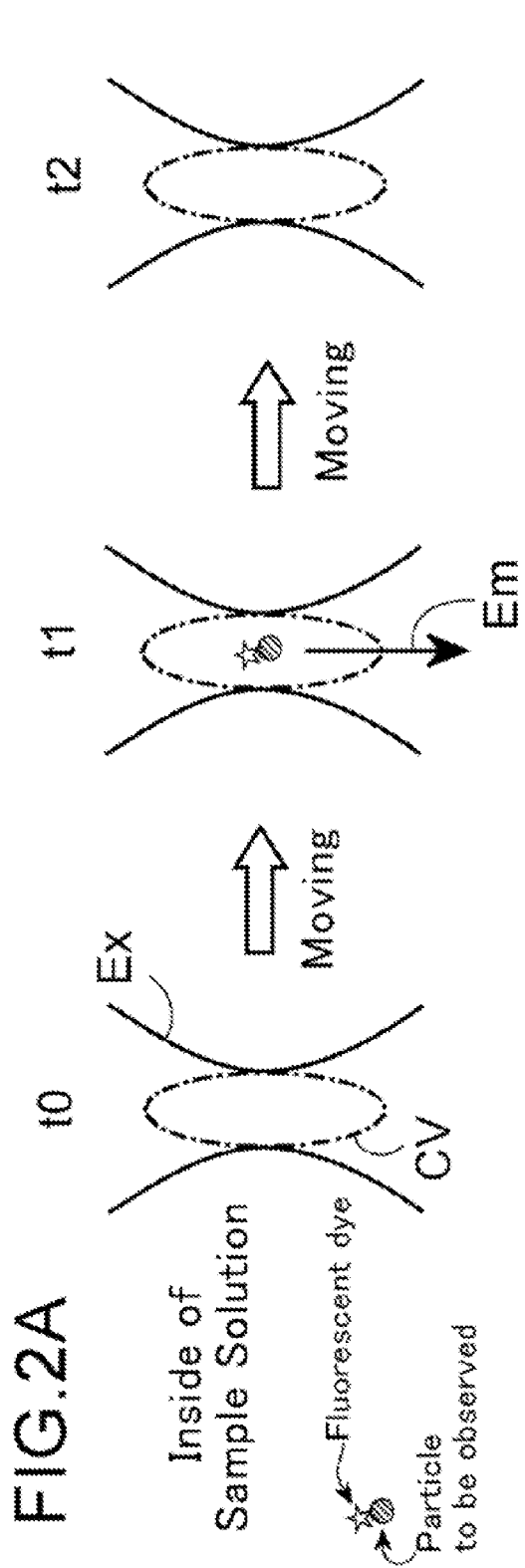
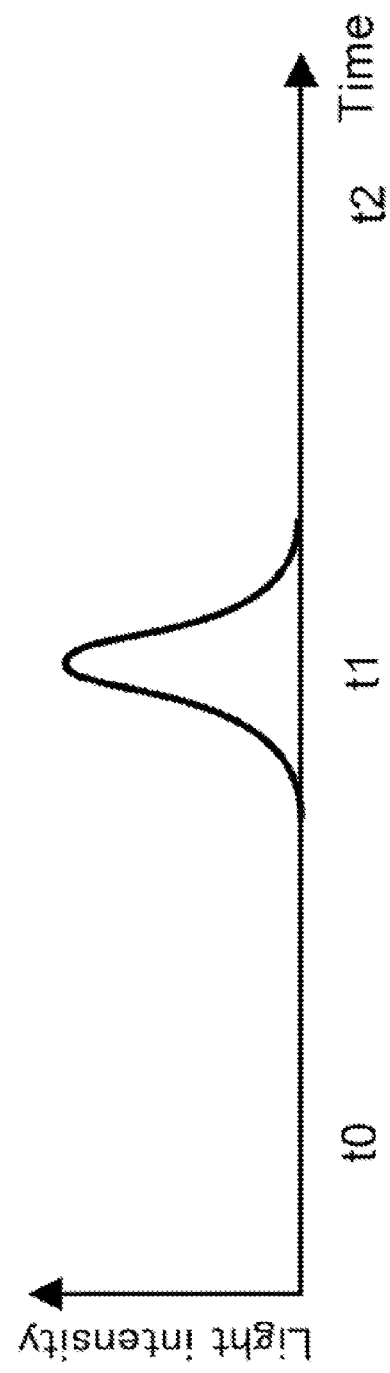
FIG.2A
FIG.2B

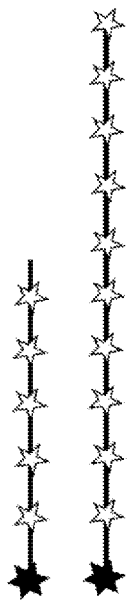
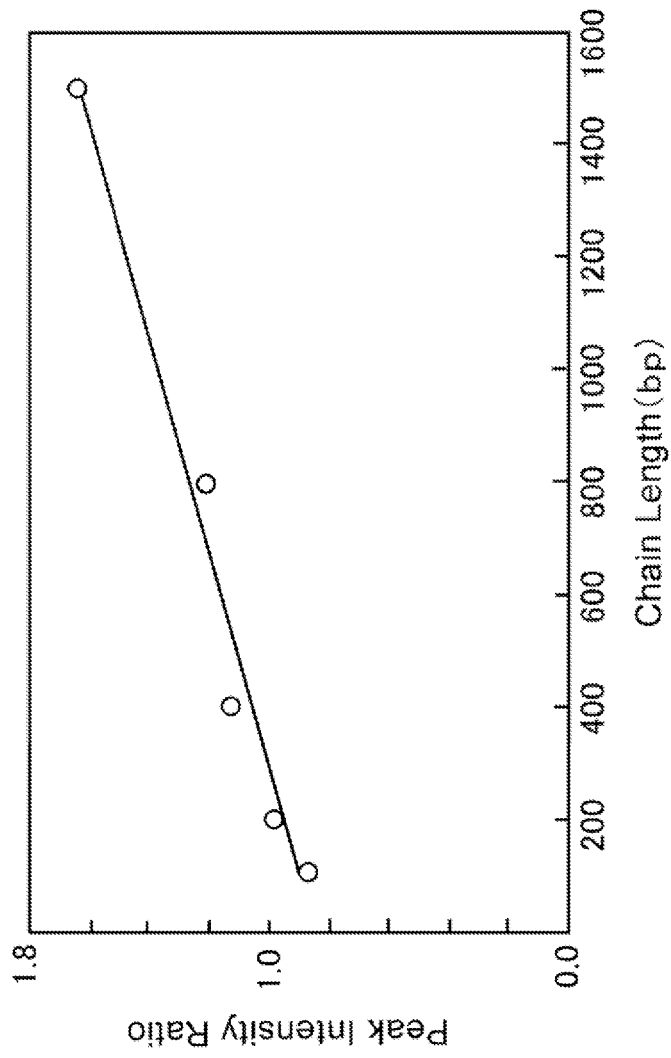
FIG.8A
FIG.8B

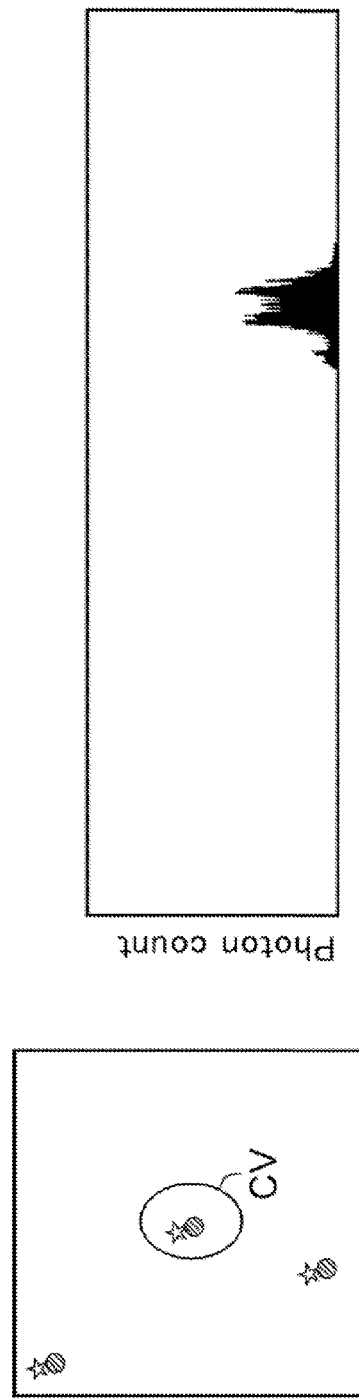

OPTICAL ANALYSIS METHOD USING THE LIGHT INTENSITY OF A SINGLE LIGHT-EMITTING PARTICLE

TECHNICAL FIELD

This invention relates to an optical analysis method capable of detecting light from a particulate object, e.g. an atom, a molecule or an aggregate thereof (Hereafter, these are called a "particle".), such as a biological molecule, for example, protein, peptide, nucleic acid, lipid, sugar chain, amino acid or these aggregate, virus and cell, etc., or a non-biological particle, dispersed or dissolved in a solution, by using an optical system, such as the optical system of a confocal microscope or a multiphoton microscope, which can detect light from a micro region in a solution, to acquire useful information in an analysis of conditions (interaction, binding or dissociating condition, etc.) of particles, and more specifically, relates to a method of detecting the light from a single particle which emits light individually, using an optical system as described above, to make it possible to conduct various optical analyses. In this regard, in this specification, a particle which emits light (hereafter, referred to as a "light-emitting particle") may be any of a particle which itself emits light and a particle to which an arbitrary light-emitting label has been attached, and the light emitted from a light-emitting particle may be fluorescence, phosphorescence, chemiluminescence, bioluminescence, scattered light, etc.

BACKGROUND ART

According to the developments in optical measurement techniques in recent years, detection and/or measurement of faint light at a single photon or single fluorescent molecule level have become possible by using an optical system of a confocal microscope and a super high sensitive light detection technique capable of the photon counting (single photon detection). Thus, there are variously proposed devices or methods of performing detection of a characteristic, an intermolecular interaction, a binding or dissociating reaction of a biological molecule, etc. by means of such a faint light measurement technique. For example, in Fluorescence Correlation Spectroscopy (FCS, see e.g. patent documents 1-3 and non-patent documents 1-3), by means of the optical system of a laser confocal microscope and a photon counting technique, there is performed the measurement of fluorescence intensity of fluorescent molecules or fluorescently labeled molecules (fluorescent molecules, etc.), entering into and exiting out of a micro region (the focal region to which the laser light of the microscope is condensed, called a "confocal volume") in a sample solution, and based on the average dwell time (translational diffusion time) of the fluorescent molecules, etc. and the average value of the number of the dwelling molecules in the micro region, determined from the autocorrelation function value of the measured fluorescence intensity, there are achieved the acquisition of information, such as the motion speed, the size or the concentration of the fluorescent molecules, etc., and/or the detection of various phenomena, such as a change of a molecular structure or size, a binding or dissociative reaction or dispersion and aggregation of molecules. Further, in Fluorescence Intensity Distribution Analysis (FIDA, e.g. patent document 4, non-patent document 4) or Photon Counting Histogram (PCH, e.g. patent document 5), there is generated a histogram of fluorescence intensity of fluorescent molecules, etc., entering into and exiting out of a confocal volume, measured similarly to FCS: and the average value of the characteristic brightness of the fluorescent molecules, etc. and the average number of molecules dwelling in the confocal volume are calculated by fitting a statistical model formula to the distribution of the histogram, so that, based on the information thereof, the structure or size changes, binding or dissociative conditions or dispersion and aggregation conditions of molecules can be estimated. In addition, in patent documents 6 and 7, there are proposed methods of detecting fluorescent substances based on a time progress of fluorescence signals of a sample solution measured using the optical system of a confocal microscope. Patent document 8 has proposed a signal calculation processing technique for measuring faint light from fluorescent fine particles flowing through a flow cytometer or fluorescent fine particles fixed on a substrate by a photon counting technique to detect the existences of the fluorescent fine particles in the flow or on the substrate.

Especially, according to the methods employing the measurement technique of fluorescent light of a micro region using the optical system of a confocal microscope and a photon counting technique, such as FCS and FIDA, a sample amount required for the measurement may be extremely small (an amount used in one measurement is at most several tens of μL), and its concentration is extremely low as compared with the prior art, and the measuring time is also shortened extremely (In one measurement, a measuring process for time of order of seconds is repeated several times.). Thus, those techniques are expected to be a strong tool enabling an experiment or a test at low cost and/or quickly in comparison with conventional biochemical methods, especially in conducting an analysis of a rare or expensive sample often used in the field of the medical or biological research and development or in conducting tests of a large number of specimens, such as sick clinical diagnosis or the screening of bioactive substances.

PRIOR TECHNICAL DOCUMENTS

Patent Documents

Patent document 1: Japanese Patent laid-open publication No. 2005-098876
Patent document 2: Japanese Patent laid-open publication No. 2008-292371
Patent document 3: Japanese Patent laid-open publication No. 2009-281.831
Patent document 4: Japanese Patent No. 4023523
Patent document 5: WO 2008-080417
Patent document 6: Japanese Patent laid-open publication No. 2007-20565
Patent document 7: Japanese Patent laid-open publication No. 2008-116440
Patent document 8: Japanese Patent laid-open publication No. 4-337446

Non-Patent Documents

Non-patent document 1: Masataka Kaneshiro; "Protein, Nucleic acid, Enzyme" Vol. 44, No. 9, pages 1431-1438, 1999.
Non-patent document 2: F. J. Meyer-Alms; "Fluorescence Correlation Spectroscopy" edt. R. Rigler, Springer, Berlin, pages 204-224, 2000.
Non-patent document 3: Noriko Kato, et al. "Gene medicine", Vol. 6, No. 2, pages 271-277.
Non-patent document 4: P. Kask, K. Palo, D. Ullmann, K. Gall PNAS 96, 13756-13761 (1999)

SUMMARY OF INVENTION

Technical Problem

In the above-mentioned optical analysis technique using the optical system of a confocal microscope and a photon counting technique, such as FCS, and FIDA, although the measured light is the light emitted from single or several fluorescent molecules, there are conducted in the analysis of the light the statistical procedures for the calculating of the fluorescence intensity fluctuation, etc., such as the computation of the autocorrelation function or the fitting to the histogram of fluorescence intensity data measured in time series, and therefore the signal of the light from an individual fluorescent molecule is not seen or analyzed. That is, in these optical analysis techniques, through the statistical processing of the signals of the lights from a plurality of fluorescent molecules, etc., statistical average characteristics of the fluorescent molecules, etc. will be detected. Thus, in order to obtain a statistically significant result in these optical analysis techniques, the concentration or number density of a fluorescent molecule, etc. to be an observation object in the sample solution should be at a level so that fluorescent molecules, etc. of the number enabling a statistical process will enter in and exit from a micro region in one measuring term of a length of order of seconds in an equilibrium, preferably so that about one fluorescent molecule, etc. will be always present in the micro region. Actually, since the volume of a confocal volume is about 1 fL, the concentration of a fluorescent molecule, etc. in a sample solution used in the above-mentioned optical analysis technique is typically at the level of 1 nM or more, and at much less than 1 nM, there is produced a term in which no fluorescent molecules, etc. are present in the confocal volume so that no statistically significant analysis result will be obtained. On the other hand, in the detection methods of fluorescent molecules, etc. described in patent documents 6-8, no statistical computation processes of fluorescence intensity fluctuation are included so that fluorescent molecules, etc. even at less than 1 nM in a sample solution can be detected, but, it has not been achieved to compute quantitatively the concentration or number density of a fluorescent molecule, etc. moving at random in a solution.

Then, in Japanese patent application No. 2010-044714 and PCT/JP2011/63481, Applicant of the present application has proposed an optical analysis technique based on a new principle which makes it possible to observe quantitatively a condition or characteristic of a light-emitting particle in a sample solution where the concentration or number density of the light-emitting particle to be an observation object is lower than the level at which the optical analysis techniques including statistical procedures, such as FCS and FIDA, etc. are used. In this new optical analysis technique, briefly, there is used an optical system which can detect light from a micro region in a solution, such as an optical system of a confocal microscope or a multiphoton microscope, similarly to FCS, FIDA, etc., and additionally, the position of the micro region, i.e. the detection region of light, (called "light detection region" in the following) is moved in the sample solution, namely, the inside of the sample solution is scanned with the micro region, and when a light-emitting particle, dispersed and moving at random in the sample solution, crosses the inside of the micro region, the light emitted from the light-emitting particle is detected, and thereby each of the light-emitting particles in the sample solution is detected individually so that it becomes possible to perform the counting of light-emitting particles and the acquisition of the information about the concentration or number density of the light-emitting particle in the sample solution. According to this new optical analysis technique (called a "scanning molecule counting method", hereafter.), not only a sample amount necessary for measurement may be small (for example, about several 10 μL) and the measuring time is short similarly to optical analysis techniques, such as FCS and FIDA, but also, it becomes possible to detect the presence of a light-emitting particle and to quantitatively detect its characteristic, such as a concentration or a number density, at a lower concentration or number density, as compared with the cases of optical analysis techniques, such as FCS and FIDA.

By the way, among the above-mentioned optical analysis techniques using the optical system of the confocal microscope and the photon counting technique, according to FIDA, the fluorescence intensity per single light-emitting particle can be estimated, and therefore, it is possible to characterize a light-emitting particle with the magnitude of the fluorescence intensity per the single light-emitting particle (characterization) and to make "identification of a light-emitting particle" in a sample solution (the specifying or identifying of a kind of light-emitting particle or the confirming or determining of what kind of light-emitting particle or which light-emitting particle a detected light-emitting particle is) based on its characterization. For instance, in a case of performing FIDA with attaching a fluorescent label to two particles, where it is unknown whether or not the two particles bind with each other, since the magnitude of the fluorescence intensity of a light-emitting particle moving as one unit can be detected in accordance with FIDA, it can be determined from the magnitude of the fluorescence intensity whether the two particles exist as separate, single units or as a combination (The fluorescence intensity of a combination becomes a double of the fluorescence intensity of a single unit.). However, in the case of FIDA, as noted, the fluorescence intensity per single light-emitting particle is determined through a statistical procedure, such as the fitting to the histogram of time series fluorescence intensity data, and thus, the concentration of the light-emitting particle required for the observation object in a sample solution is usually at about 1 nM, and it is difficult to obtain an accurate result when the concentration of the light-emitting particle is much less than that. For example, in a case that a binding action is weak or the number of total particles is small in the test of a binding reaction of two particles as the above, only a small number of combinations are formed, and accordingly, it is possible that the information on the light from the combinations is buried in a statistical procedure. (i.e., it is possible that the information would not be detected.).

Contrary to the FIDA, according to the above-mentioned scanning molecule counting method, even when the concentration of a light-emitting particle to be an observation object in a sample solution is substantially lower than a level well measurable in FIDA, the measurement of the light intensity emitted by a single light-emitting particle is possible. In the scanning molecule counting method, on a time-series light intensity data, a signal of the light intensity change having a crest shaped or almost bell shaped profile corresponding to the light emitted by a single light-emitting particle when entering into the light detection region is detected individually, and therefore, in that time, by measuring the intensity of each signal individually, the light intensity emitted from the single light-emitting particle will be measured, and the characterization of the light-emitting particle or the identification of the light-emitting particle seems achievable based on the light intensity emitted by the single light-emitting particle.

However, it is difficult to perform a characterization of a light-emitting particle and an identification of a light-emitting particle, using the absolute value of the emitted light intensity of a single light-emitting particle measured in the scanning molecule counting method as it is. In the actual light detection region, i.e., confocal volume, of the optical system of a confocal microscope or a multiphoton microscope, the excitation light intensity is not uniform, which, usually, has a bell-shaped distribution whose peak is positioned on the approximate center of the light detection region. Thus, in the light measurement process with the light detection region scanning, the measured, emitted light intensity differs depending upon the place through which a light-emitting particle passes in the light detection region, resulting in the scattering in the absolute value of the emitted light intensity from the same kind of light-emitting particle, and also, no distinctions are made between the intensity of the signal acquired when a particle having weak emitted light intensity passes through a site having a strong excitation light intensity and the intensity of the signal acquired when a particle having strong emitted light intensity passes through a site of a weak excitation light intensity. That is, the absolute value of the emitted light intensity measured in the scanning molecule counting method is not a characteristic value of a light-emitting particle, and consequently, a novel way is needed in trying to use the emitted light intensity of a single light-emitting particle for the characterization or identification of the light-emitting particle.

Thus, one object of the present invention is to provide a new optical analysis method which enables a characterization of a light-emitting particle or an identification of a light-emitting particle based on the emitted light intensity of a single light-emitting particle in a sample solution of a light-emitting particle of a concentration lower than a level well measurable by FIDA.

Moreover, another object of the present invention is to provide a new optical analysis method which determines a quantity peculiar to a light-emitting particle using the emitted light intensity of a single light-emitting particle measured individually to enables a characterization or an identification of a particle in the scanning molecule counting method.

Solution to Problem

According to the present invention, the above-mentioned object is achieved by a method of detecting and analyzing light from a light-emitting particle dispersed and moving at random in a sample solution using an optical system of a confocal microscope or a multiphoton microscope, characterized by comprising steps of: preparing the sample solution containing a light-emitting particle having a first light-emitting site and a second light-emitting site which has a different emission wavelength from that of the first light-emitting site; moving a position of a light detection region of the optical system in the sample solution by changing an optical path of the optical system; measuring light intensity of the first light-emitting site and light intensity of the second light-emitting site from the light detection region individually and simultaneously with moving the position of the light detection region in the sample solution to individually generate light intensity data; individually detecting a signal indicating light of a single light-emitting particle in the light intensity data; and identifying a single light-emitting particle with a ratio of the light intensity of the first light-emitting site and the light intensity of the second light-emitting site in respective signals simultaneously generated on the light intensity data of the first light-emitting site and the light intensity data of the second light-emitting site. In this structure, "a light-emitting particle dispersed and moving at random in a sample solution" may be a particle, such as an atom, a molecule or an aggregates of these, which is dispersed or dissolved in a sample solution and emits light, and it may be an arbitrary particulate matter making the Brownian motion freely in a solution without being fixed on a substrate, etc. The light-emitting particle is typically a fluorescent particle, but may be a particle which emits light by phosphorescence, chemiluminescence, bioluminescence, light scattering, etc. The "light detection region" of the optical system of the confocal microscope or multiphoton microscope is the micro region where light is detected in those microscopes, which region corresponds to the region to which illumination light is condensed when the illumination light is given from an objective (Especially in a confocal microscope, this region is determined in accordance with the spatial relationship of an objective and a pinhole. For a light-emitting particle which emits light without illumination light, for example, a molecule which emits light according to chemiluminescence or bioluminescence, no illumination light is required in the microscope.). Further, in the followings in this specification, "a signal" means "a signal expressing light from a light-emitting particle" unless noted otherwise.

As understood from the above, in the basic structure of the present invention, i.e., the scanning molecule counting method, the measurement of light intensity is sequentially performed while the position of a light detection region is moved in the sample solution, namely, while the inside of the sample solution is scanned with the light detection region. Then, when the moving light detection region encompasses a randomly moving light-emitting particle, the light from the light-emitting particle is detected by the light detecting portion, and thereby, the existence of one particle will be detected. And, in the time series light intensity data indicating sequentially detected light, a signal indicating light from a light-emitting particle is individually detected, and thereby, the individual existences of light-emitting particles are detected one by one, and accordingly, diverse information on the condition of a particle in the solution will be acquired. In that case, as already noted, the light intensity from a light-emitting particle differs depending on the place where the particle has crossed in the light detection region, and is not a value peculiar to the light-emitting particle, and thus, it is difficult to characterize the light-emitting particle with the absolute value of the light intensity of the light-emitting particle.

Thus, in the present invention, a particle which possesses at least two light-emitting sites (the first and second light-emitting sites) having mutually different emission wavelengths is prepared as a light-emitting particle, and the lights from these light-emitting sites are measured separately, and the ratio of the light intensity of the first light-emitting site and the light intensity of the second light-emitting site is seen. Since, usually, both the light intensity of the first light-emitting site and the light intensity of the second light-emitting site increase or decrease together with increase or decrease of the excitation light intensity, the ratio of the light intensity of the first light-emitting site and the light intensity of the second light-emitting site in a single light-emitting particle is invariable against the excitation light intensity change, irrespective of the place in the light detection region through which the light-emitting particle passes. Therefore, since it is thought that the ratio of the light intensity of the first light-emitting site and the light intensity of the second light-emitting site is a value peculiar to a light-emitting particle, a light-emitting particle can be characterized with this ratio, and based on the characterization, the identification of the light-emitting particle will be achieved.

In the above-mentioned structure of the present invention, in a case that light-emitting particles whose kinds, sizes or characteristics are mutually different, or light-emitting particles to be mutually discriminated are present in a sample solution, light-emitting particles may be so prepared that the first light-emitting site will be a common light-emitting site which is common in at least a part of light-emitting particles in a sample solution while the second light-emitting site becomes a specific light-emitting site with which the respective light-emitting particle will be characterized. According to this structure, for the light-emitting particles having the common light-emitting site, it becomes possible to discriminate them from one another with the ratio of the light intensity from the common light-emitting site and the light intensity from the specific light-emitting site. In this regard, the common light-emitting site may be attached to all light-emitting particles to be observed in a sample solution, or a light-emitting site common to all light-emitting particles to be observed in a sample solution may be employed as the common light-emitting site. In that case, it becomes possible to discriminate mutually all light-emitting particles to be observed in a sample solution with the ratio of the light intensity of the common light-emitting site and the light intensity of the specific light-emitting site, which will be advantageous in various analyses.

In a manner of the above-mentioned identification of a light-emitting particle, for example, a kind of single light-emitting particle may be identified with the ratio of the light intensity of the first light-emitting site and the light intensity of the second light-emitting site. Namely, by preparing light-emitting particles so that the ratio of the light intensity of the first light-emitting site and the light intensity of the second light-emitting site will differ according to the kind of light-emitting particle, it becomes possible to identify with the ratio of the intensities the kind of light-emitting particle corresponding to each signal. This structure may be achieved, for example, by making the kind or number of the second light-emitting site(s) in a light-emitting particle different depending upon the kind of light-emitting particle. Further, especially, the size of a single light-emitting particle may be identified with the ratio of the light intensity of the first light-emitting site and the light intensity of the second light-emitting site. As seen in an embodiment described later, in a case of a light-emitting particle of a type that the number of the second light-emitting sites of a single light-emitting particle increases as its size becomes large, since the light intensity from the second light-emitting site changes with the size of a light-emitting particle relatively to the light intensity of the first light-emitting site, the size of the light-emitting particle can also be determined according to the increase or decrease in the ratio of the light intensity of the first light-emitting site and the light intensity of the second light-emitting site(s).

In the above-mentioned structure, the detection of a signal corresponding to a single light-emitting particle on light intensity data may be done based on the shape of the signal. In one embodiment, typically, when a pulse form signal which has a higher intensity than a predetermined threshold value is detected, its signal is a signal corresponding to one light-emitting particle, and thus, it may be judged that one light-emitting particle was present in the light detection region in the generation period of the signal. The detection of signals simultaneously generated on two light intensity data may be performed, for example, in a manner that when the generation period of a signal indicating light of a light-emitting particle in the light intensity data of the first light-emitting site overlaps the generation period of a signal indicating light of a light-emitting particle in the light intensity data of the second light-emitting site, those signals are detected as simultaneously generated signals, or in a manner that when the difference between the time of the peak of a signal in the light intensity data of the first light-emitting site and the time of the peak of a signal in the light intensity data of the second light-emitting site is smaller than a predetermined value, those signals are detected as simultaneously generated signals.

In this regard, in the above-mentioned inventive structure, the number of identified single light-emitting particles may be counted (counting of particles). In that case, by associating the number of the identified light-emitting particles with the moving amount of the position of the light detection region, the information on the number density or concentration of the light-emitting particle in the sample solution will be acquired. Especially, by determining the whole volume of the moving track of the position of the light detection region by an arbitrary method, for example, by moving the position of the light detection region at a predetermined speed, the number density or concentration of the light-emitting particle can be concretely computed. Of course, instead of determining directly the absolute number density value or concentration value, the relative ratio of the number density or concentration to a plurality of sample solutions or a standard sample solution to be a reference of a concentration or a number density may be computed. It should be understood that, according to the present invention, light-emitting particles corresponding to individual (simultaneously generated) signals are identified, and thereby, counting the number of light-emitting particles separately by the kind, the characteristic or the size of light-emitting particle, and/or determining its concentration or number density can be made, and therefore, the inventive method may be used advantageously in analyses of various intermolecular interaction, binding or dissociating conditions.

Moreover, with respect to the step of moving the position of the light detection region in the above-mentioned inventive structure, the moving speed of the position of the light detection region in the sample solution is appropriately changed based on the characteristic or the number density or concentration of the light-emitting particle in the sample solution. As understood by ones ordinarily skilled in the art, the condition of detected light from the light-emitting particle may change in accordance with its characteristic, number density or concentration in the sample solution. Especially, when the moving speed of the light detection region becomes quick, the amount of light obtained from one light-emitting particle will be reduced, and therefore it is preferable that the moving speed of the light detection region can be changed appropriately so that the light from one light-emitting particle can be measured precisely or with sufficient sensitivity.

Furthermore, with respect to the above-mentioned step of moving the position of the light detection region, the moving speed of the position of the light detection region in the sample solution is preferably set to be higher than the diffusional moving velocity of a light-emitting particle (the average moving speed of a particle owing to the Brownian motion). As explained above, in the inventive method, the light detection region detects the light emitted from a light-emitting particle, so that the light-emitting particle will be detected individually. However, when a light-emitting particle moves at random owing to the Brownian motion to move into and out of the light detection region multiple times, it is possible that the signal from one light-emitting particle (showing its existence) will be detected multiple times, and therefore it would become difficult to make the existence of one light-emitting particle associated with the detected signal. Then, as described above, the moving speed of the light detection region is set higher than the diffusional moving velocity of the light-emitting particle, and thereby it becomes possible to make one light-emitting particle correspond to one signal. In this regard, since the diffusional moving velocity differs depending upon light-emitting particles, it is preferable that the moving speed of the light detection region can be changed appropriately according to the characteristics (especially, the diffusion constant) of the light-emitting particle as described above.

The changing of the optical path of the optical system for moving the position of the light detection region may be done in an arbitrary way. For example, the position of the light detection region may be changed by changing the optical path using a galvanomirror employed in the laser scan type optical microscope. The movement track of the position of the light detection region may be set arbitrarily, for example, which is selectable from circular, elliptical, rectangular, straight and curvilinear ones. In this connection, in the present invention, since the position of the light detection region is moved by changing the optical path of an optical system, the movement of the light detection region is quick without substantial generation of mechanical vibration and hydrodynamic effect in the sample solution, and therefore, the measurement of light can be performed under a stable condition without dynamic action affecting the light-emitting particle in the sample solution (without artifact) (For example, when a flow is generated in the sample, not only making the flow velocity always uniform is difficult, but also the device structure would become complicated, and furthermore, not only the required sample amount is substantially increased, but also it is possible that light-emitting particles or other substances in a solution would deteriorate or be denaturalized by the hydrodynamic action of the flow.). Further, since no structure for flowing a sample solution is required, the measurement and analysis can be conducted with a small amount of the sample solution (at the level of one to several tens of µL) similarly to FCS and FIDA, etc.

The inventive method is used, typically, for an analysis of a condition in a solution of a biological particulate object, such as a biological molecule, e.g. a protein, a peptide, a nucleic acid, a lipid, a sugar chain, an amino acid or these aggregate, a virus and a cell, etc., but it may be used for an analysis of a condition in a solution of a non-biological particle (for example, an atom, a molecule, a micelle, a metallic colloid, etc.), and it should be understood that such a case belongs to the scope of the present invention also.

Effect of Invention

Generally, in the inventive method, noticing that the ratio of the light intensities emitted from two light-emitting sites of a single light-emitting particle is invariable against the change of an excitation light intensity, namely, that the ratio can be a characteristic peculiar to a light-emitting particle irrespective of the place through which the light-emitting particle passes in the light detection region of the optical system of a confocal microscope or a multiphoton microscope, the identification of a light-emitting particle is made for each signal of the light of a single light-emitting particle detected in the scanning molecule counting method by means of the above-mentioned ratio of the light intensities. As already noted, the scanning molecule counting method where the light from a single light-emitting particle is individually detected is performed without statistical procedure such as computing fluorescence intensity fluctuation and applicable for a sample solution in which the number density or concentration of a particle is significantly lower than the level required for optical analysis techniques, such as FCS and FIDA, and further, it can be said that the inventive method which enables identification of a light-emitting particle in the scanning molecule counting method makes it possible to perform the identification of a single light-emitting particle at a level lower than the concentration range analyzable by FIDA. Further, according to the present invention, the characterization and identification of a single light-emitting particle become achievable in a scanning molecule counting method, and thus, the discrimination of light-emitting particles of mutually different kinds, characteristics or sizes is also achievable, and consequently, it is expected that the application range of the scanning molecule counting method will be expanded for observation and analysis for a light-emitting particle at an extremely low concentration or a comparatively weak intermolecular interaction. For instance, even in a case that an interaction of light-emitting particles of two or more kinds in a sample solution is weak so that only a minute amount of combinations of those light-emitting particles will be formed (for example, at a level where a detection is difficult in FIDA), the inventive method will be advantageously used for the confirmation of the existence, the counting, etc. of the combination(s).

Other purposes and advantages of the present inventions will become clear by explanations of the following preferable embodiments of the present invention.

BRIEF DESCRIPTIONS OF DRAWINGS

Figure 1B:
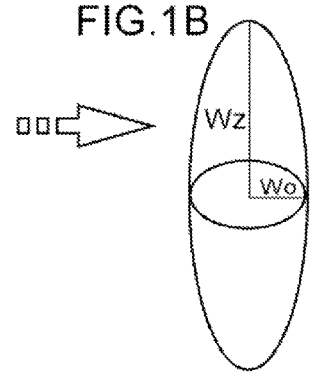
Figure 1C:
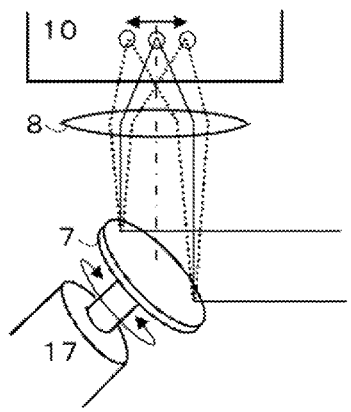

FIG. 1A is a schematic diagram of the internal structure of the optical analysis device with which the present invention is performed. FIG. 1B is a schematic diagram of a confocal volume (a light detection region of a confocal microscope). FIG. 1C is a schematic diagram of the mechanism for changing the direction of the mirror 7 to move the position of a light detection region in a sample solution.

FIGS. 2A and 2B are a schematic diagram explaining the principle of the light detection and a schematic diagram of the variation of the measured light intensity with time in the scanning molecule counting method to which the inventive method is applied, respectively.

Figure 3A:
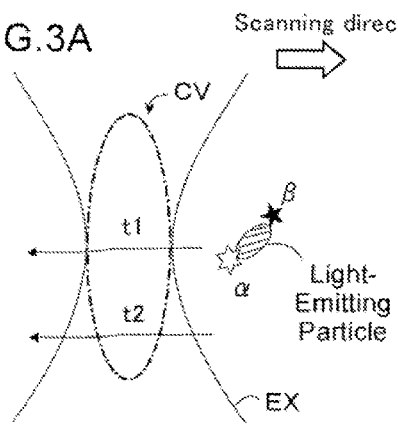
Figure 3B:
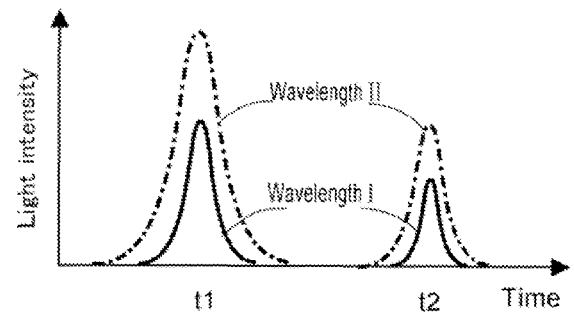
Figure 3C:
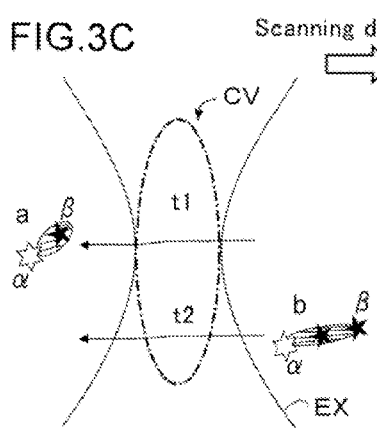
Figure 3D:
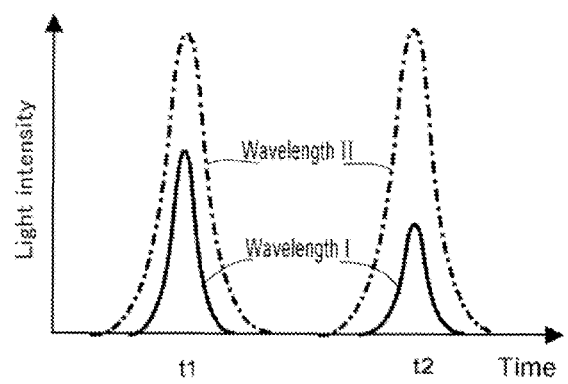
Figure 3E:
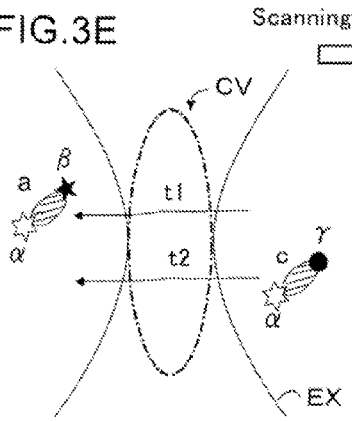
Figure 3F:
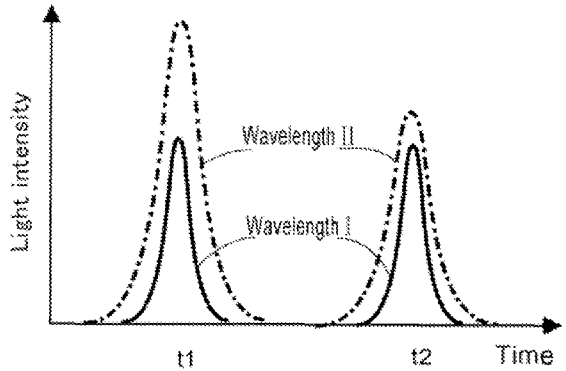

FIGS. 3A-3F are drawings explaining the principle in the identification of a light-emitting particle with the ratio of light intensities of light-emitting sites of two or more kinds on a single light-emitting particle in accordance with the inventive method. FIG. 3A and FIG. 3B are a model figure of a condition of a molecule and time changes of light intensities in cases that a light-emitting particle passes through different places in the light detection region; FIG. 3C and FIG. 3D are a model figure of conditions of molecules and time changes of light intensities in cases that the number of light-emitting sites of one kind differs depending upon light-emitting particles; and FIG. 3E and FIG. 3F are a model figure of conditions of molecules and time changes of light intensities in cases that the kind of the light-emitting site of one kind differs depending upon light-emitting particles.

Figure 4:
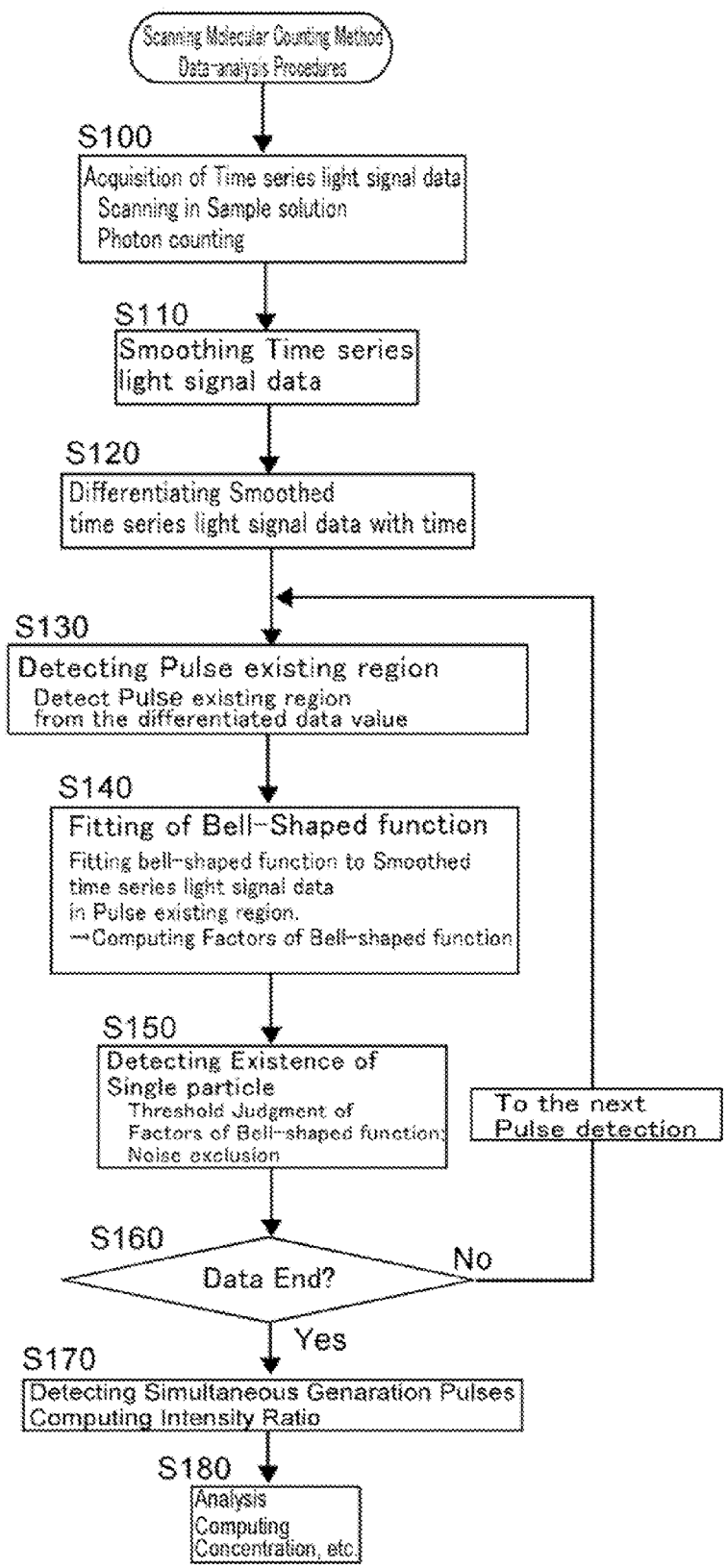

FIG. 4 is a drawing showing in the form of a flow chart the procedures of the scanning molecule counting method of performing a measurement of light and calculation of the intensity ratio of lights from two or more light-emitting sites in accordance with the inventive method.

Figure 5A:
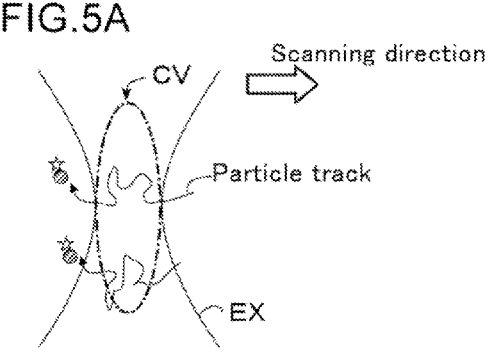
Figure 5B:
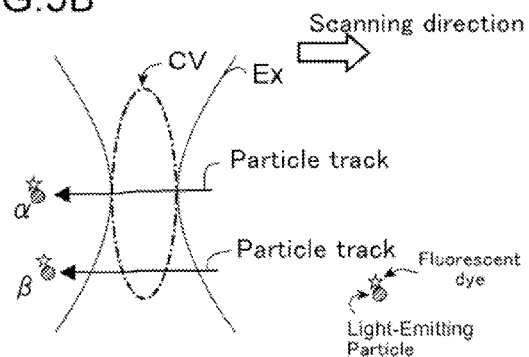
Figure 5C:
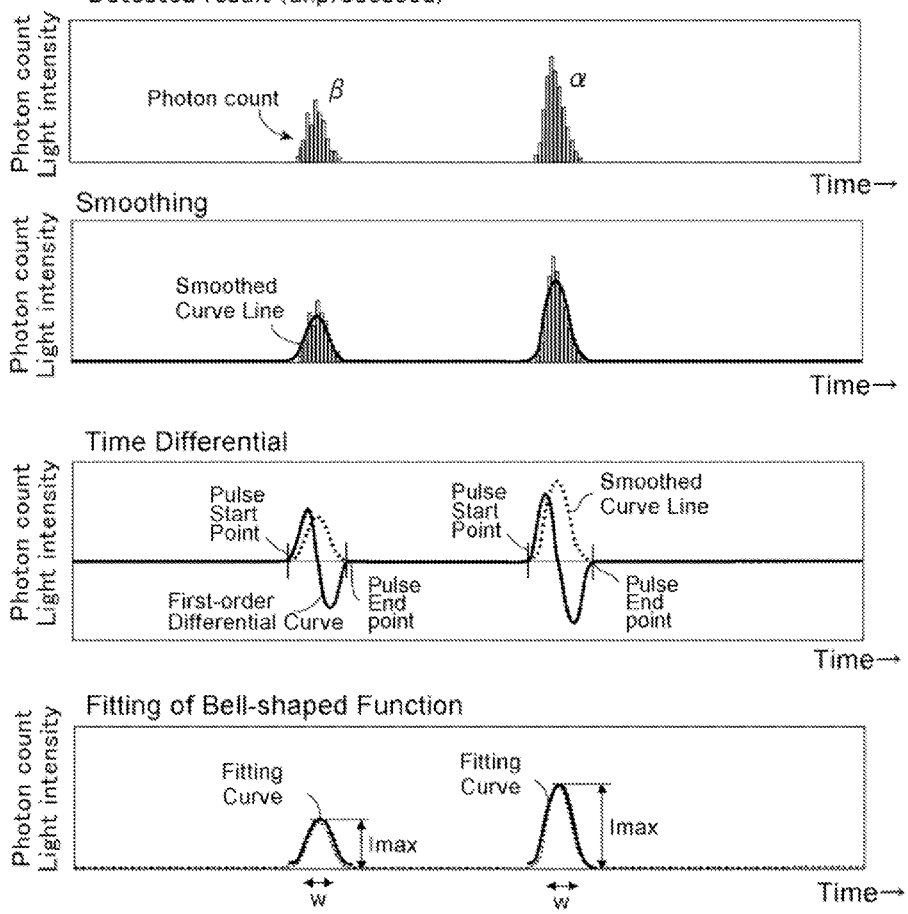

FIGS. 5A and 5B are drawings of models in a case that a light-emitting particle crosses a light detection region owing to Brownian motion and in a case that a light-emitting particle crosses a light detection region by moving the position of the light detection region in a sample solution at a velocity quicker than the diffusional moving velocity of the light-emitting particle. FIG. 5C shows drawings explaining the example of the signal processing step of the detected signals in the procedure for detecting the existence of a light-emitting particle from the measured time series light intensity data (change in time of photon count) in accordance with the scanning molecule counting method.

Figure 6A:
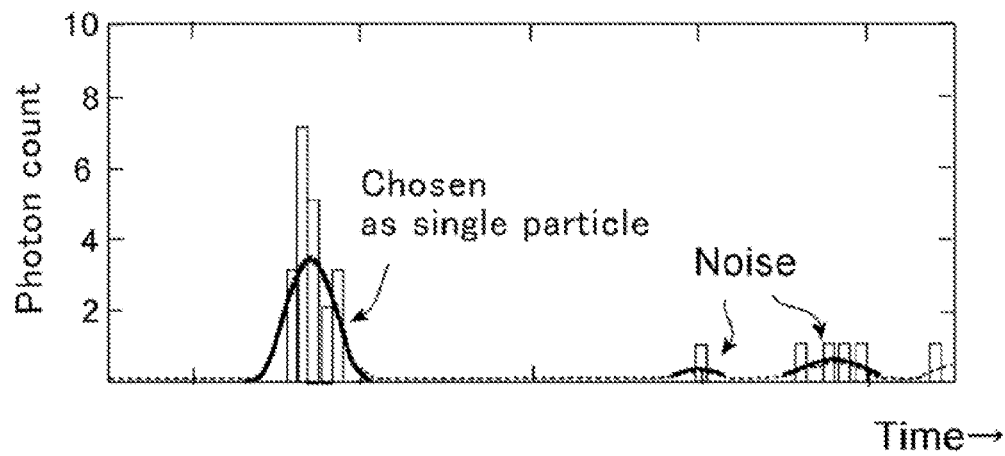
Figure 6B:
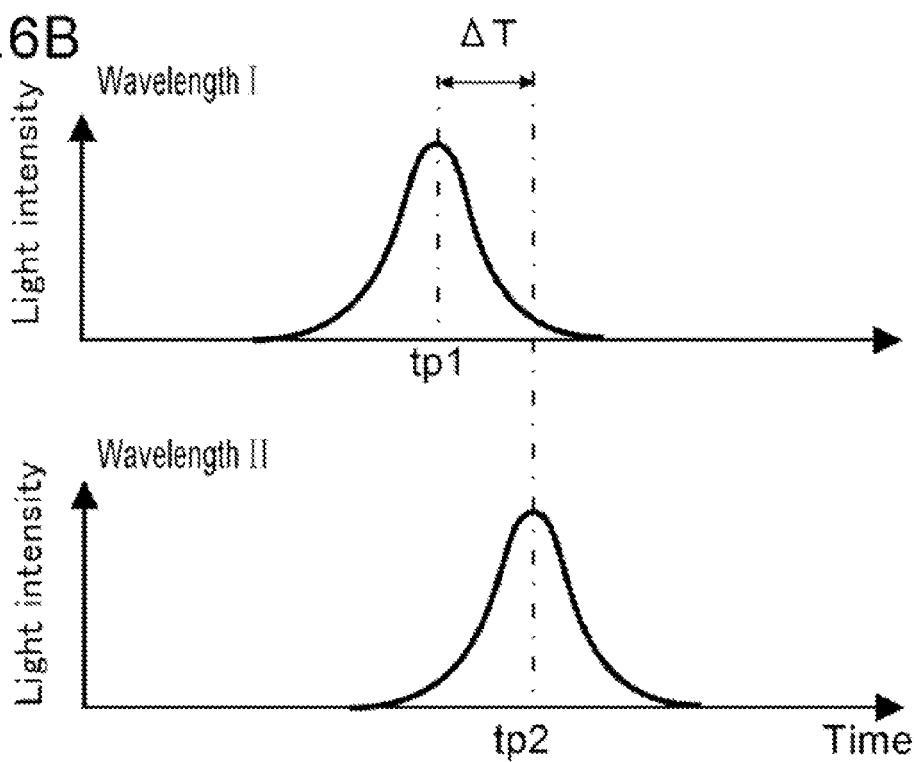

FIG. 6A shows examples of measured photon count data (bar graph); curves obtained by carrying out the smoothing of the data (dotted line); and Gauss functions fitted on the pulse existing regions (solid line). In the drawing, the signals attached with "noise" are disregarded as signals due to noises or a contaminant. FIG. 6B is a drawing explaining the process of judging whether or not signals generated on the time series light intensity data of different wavelength bands have been simultaneously generated.

Figure 7A:
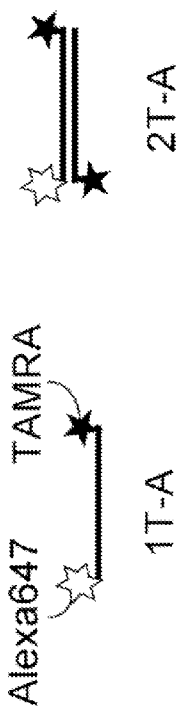
Figure 7B:
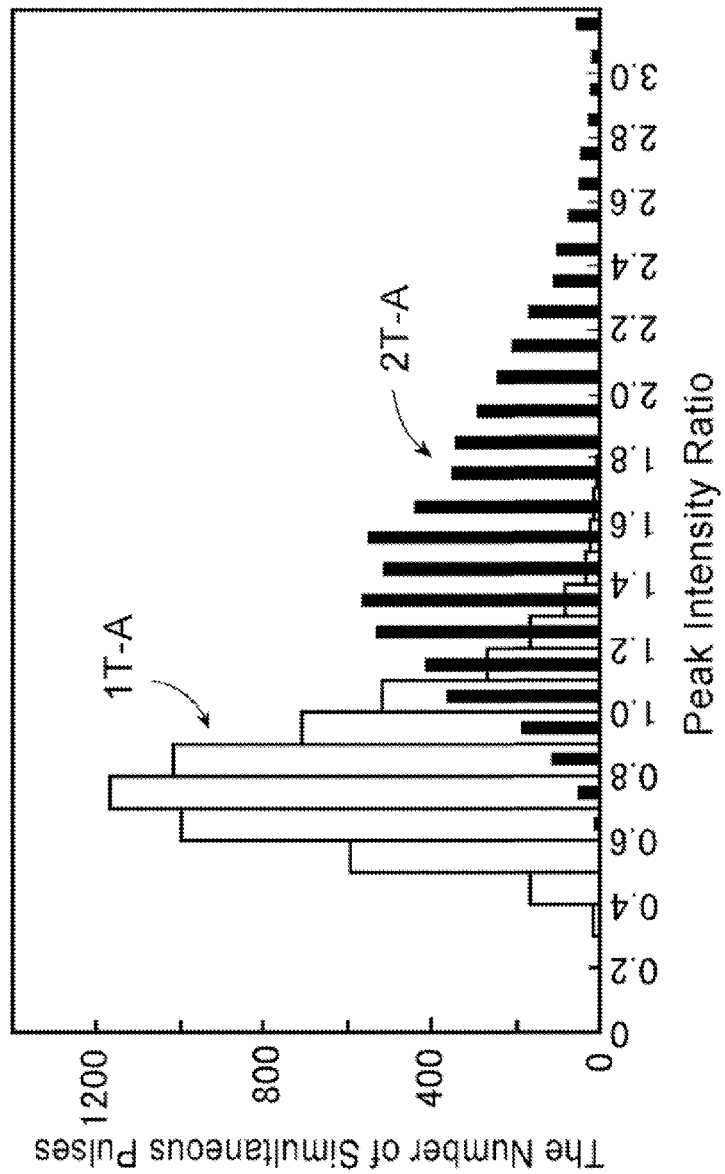

FIG. 7A are model drawings of oligonucleotide molecules (1 T-A, 2 T-A) to which two kinds of fluorescent label have been attached, observed by a scanning molecule counting method performed in accordance with the inventive method (embodiment 1), and FIG. 7B is a drawing which shows the generation frequencies (the number of simultaneous generation pulses) of the ratio of fluorescence intensities of two kinds (peak intensity ratio) in the observed simultaneous generation pulses of 1 T-A and 2 T-A in the form of a bar graph.

FIG. 8A are model drawings of DNA to which two kinds of fluorescent labels have been attached whose number of fluorescent labels of one kind differs depending upon chain lengths, observed by the scanning molecule counting method performed in accordance with the inventive method (embodiment 2), and FIG. 8B is a graph showing change of the ratio (peak intensity ratio) of fluorescence intensities of two kinds against the chain length of DNA.

FIGS. 9A-9B show examples of the time variation of the photon count (light intensity) obtained in a conventional optical analysis technique computing fluorescence intensity fluctuation, where FIG. 9A shows a case that the particle concentration is at a level providing a sufficient precision in the measurement, and FIG. 9B shows a case that the particle concentration in a sample is significantly lower than the case of (A).

EXPLANATIONS OF REFERENCE NUMERALS

1 - - - Optical analysis device (confocal microscope)
2 - - - Light source
3 - - - Single mode optical fiber
4 - - - Collimating lens
5, 14a - - - Dichroic mirror
6, 7, 11 - - - Reflective mirror
8 - - - Objective
9 - - - Micro plate
10 - - - Well (sample solution container)
12 - - - Condenser lens
13 - - - Pinhole
14 - - - Barrier filter
15 - - - Multi-mode optical fiber
16 - - - Photodetector
17 - - - Mirror deflector
17a - - - Stage position changing apparatus
18 - - - Computer

DESCRIPTION OF EMBODIMENTS

In the followings, preferable embodiments of the present invention are described in detail.

Structure of Optical Analysis Device

In the basic structure, the method according to the present invention can be realized with an optical analysis device constructed by associating the optical system of a confocal microscope and a photodetector, enabling FCS, FIDA, etc. In this connection, in the inventive method, especially, the measurement of the lights of two or more mutually different wavelength bands is performed, and thus, the device which can measure the lights of two or more mutually different wavelength bands as illustrated schematically in FIG. 1A is used.

Concretely, referring to FIG. 1A, the optical analysis device 1 consists of an optical system 2-17 and a computer 18 for acquiring and analyzing data together with controlling the operation of each part in the optical system. The optical system of the optical analysis device 1 may be the same as the optical system of a usual confocal microscope, where laser light emitted from a light source 2 and transmitted through the inside of a single mode fiber 3 (Ex) forms light diverging to be radiated at the angle decided by an inherent NA at the emitting end of the fiber; and after forming a parallel beam with a collimator 4, the light is reflected on a dichroic mirror 5 and reflective mirrors 6 and 7, entering into an objective 8. In this regard, in order that the wavelength of excitation light can be selected appropriately in accordance with the wavelength of the light exciting a light-emitting particle, as shown in the drawing, two or more light-emitting sources (laser) may be prepared in the light source 2. When the wavelengths of the excitation light for at least two light-emitting sites of a light-emitting particle to be observed simultaneously differ from one another, lights are simultaneously emitted from two or more light-emitting sources and introduced into the objective 8.

Above the objective 8, typically, there is placed a sample container or a micro plate 9 having wells 10 arranged thereon, to which one to several tens of μL of a sample solution is dispensed, and the laser light emitted from the objective 8 is focused in the sample solution in the sample container or well 10, forming a region having strong light intensity (excitation region). In the sample solution, light-emitting particles to be observed objects, which are typically molecules to which a light emitting label such as a fluorescent dye is attached, are dispersed or dissolved, and when a light-emitting particle enters into the excitation region, the light-emitting particle is excited and emits light during dwelling in the excitation region. The emitted light (Em), after passing through the objective 8 and the dichroic mirror 6, is reflected on the mirror 11 and condensed by a condenser lens 12, and then the light passes through the pinhole 13. In this regard, as known in ones skilled in the art, the pinhole 13 is located at a conjugate position of the focal position of the objective 8, and thereby only the light emitted from the focal region of the laser light, i.e., the excitation region, as schematically shown in FIG. 1B, passes through the pinhole 13 while the light from regions other than the focal plane is blocked. The focal region of the laser light illustrated in FIG. 1B is a light detection region, whose effective volume is usually about 1-10 fL, in this optical analysis device, which is called as "confocal volume". In the confocal volume, typically, the light intensity is spread in accordance with a Gaussian type or Lorentz type distribution having the peak at the center of the region, and the effective volume is a volume of an approximate ellipsoid bordering a surface where the light intensity reduced to 1/e² of the peak intensity.

Then, the light having passed through the pinhole 13 is divided in accordance with the wavelength band in the manner that the light of a part of wavelength bands is reflected on, and the light of the remaining wavelength bands penetrates through, the dichroic mirror 14a, and each component of the divided lights transmits through the corresponding barrier filter 14 (where a light component only in a specific wavelength band is selected); and is introduced into a multimode fiber 15, reaching to the corresponding photodetector 16, and after the conversion into time series electric signals, the signals are inputted into the computer 18, where the processes for optical analyses are executed in manners explained later. For the photodetectors 16, preferably, super high sensitive photodetectors, usable for the photon counting, are used, so that the light from one light-emitting particle, for example, the faint light from one or several fluorescent dye molecule(s), can be detected.

Furthermore, in the optical system of the above-mentioned optical analysis device, there is further provided a mechanism for changing the optical path of the optical system to scan the inside of the sample solution with the light detection region, namely to move the position of the focal region i.e., the light detection region, within the sample solution. For this mechanism for moving the position of the light detection region, for example, there may be employed a mirror deflector 17 which changes the direction of the reflective mirror 7, as schematically illustrated in FIG. 1C. This mirror deflector 17 may be the same as that of a galvanomirror device equipped on a usual laser scan type microscope. Also, in order to attain a desired moving pattern of the position of the light detection region, the mirror deflector 17 is driven in harmony with the light detection of the photodetector 16 under the control of the computer 18. The movement track of the position of the light detection region may be arbitrarily selected from circular, elliptical, rectangular, straight and curvilinear ones, or a combination of these (The program in the computer 18 may be designed so that various moving patterns can be selected.). In this regard, although not illustrated, the position of the light detection region may be moved in the vertical direction by moving the objective 8 up and down. As noted, according to the structure of changing the optical path of the optical system to move the position of the light detection region instead of moving the sample solution, neither mechanical vibration nor hydrodynamic action occur substantially in the sample solution, so that it becomes possible to eliminate the influence of a dynamic action on an object to be observed, achieving the stable measurement.

Also, for an additional structure, on the stage (not shown) of the microscope, there may be provided a stage position changing apparatus 17a for moving the horizontal position of the micro plate 9, in order to change the well 10 to be observed. The operation of the stage position changing apparatus 17a may be controlled by the computer 18.

In the case that a light-emitting particle emits light by multiple photon absorption, the above-mentioned optical system is used as a multiphoton microscope. In that case, since the light is emitted only from the focal region of the excitation light (light detection region), the pinhole 13 may be removed. Further, in the case that a light-emitting particle emits light owing to a chemiluminescence or bioluminescence phenomenon without excitation light, the optical system 2-5 for generating excitation light may be omitted. When a light-emitting particle emits light owing to phosphorescence or scattered light, the above-mentioned optical system of the confocal microscope is used as it is.

The Principle of the Inventive Method

As described in the column of "Summary of invention", briefly, in the inventive method, based on the principle that, in a light-emitting particle which has at least two light-emitting sites having mutually different emission wavelengths, the ratio of the light intensities of these at least two light-emitting sites does not depend on the position of the light-emitting particle in the light detection region of a microscope, a light-emitting particle is characterized with the ratio of the light intensities from at least two light-emitting sites and thereby the identification of the light-emitting particle is conducted in the scanning molecule counting method. In the other words, it can be said that one embodiment of the present invention is the improvement of the scanning molecule counting method. In the following, the principles of the scanning molecule counting method and the inventive method are described.

1. Principle of Scanning Molecule Counting Method

Spectral analysis techniques, such as FCS, FIDA, etc., are advantageous in that the required sample amount is extremely small and a test can be performed promptly as compared with the conventional biochemical analytical techniques. However, in these spectral analysis techniques such as FCS, FIDA, etc., the concentration and characteristics of a light-emitting particle are principally computed based on the fluorescence intensity fluctuation, and therefore, in order to obtain accurate measurement results, the concentration or number density of the light-emitting particle in a sample solution should be at a level where about one light-emitting particle always exists in a light detection region CV during the fluorescence intensity measurement as schematically drawn in FIG. 9A so that significant light intensity (photon count) can be always detected in the measuring term as shown in the right-hand side of the drawing. When the concentration or number density of the light-emitting particle is lower than that, for example, at the level where the light-emitting particle rarely enters into the light detection region CV as drawn on FIG. 9B, no significant light intensity signal (photon count) would appear in a part of the measuring term as illustrated on the right-hand side of the drawing, and thus, accurate computation of light intensity fluctuation would become difficult. Also, when the concentration of the light-emitting particle is significantly lower than the level where about one light-emitting particle always exists in the inside of the light detection region during the measurement, the calculation of light intensity fluctuation would become subject to the influence of the background, and the measuring term should be made long in order to obtain the significant quantity of the light intensity data (photon count) sufficient for the calculation.

Then, in the Japanese patent application no. 2010-044714 and PCT/JP2011/53481, the applicant of the present application has proposed "Scanning molecule counting method" based on a new principle which enables the detection of characteristics of a light-emitting particle, such as its number density or concentration, even when the concentration of the light-emitting particle is lower than the level requested in the above-mentioned spectral analysis techniques, such as FCS and FIDA.

In the scanning molecule counting method, briefly speaking, as the processes to be performed, the light detection is performed together with moving the position of the light detection region CV in a sample solution, namely, scanning the inside of the sample solution with the light detection region CV by driving the mechanism (mirror deflector 17) for moving the position of the light detection region to change the optical path as schematically drawn in FIG. 2. Then, for example, as in FIG. 2A, during the moving of the light detection region CV (in the drawing, time t0-t2), when the light detection region CV passes through a region where one light-emitting particle exists (t1), light is emitted from the light-emitting particle, and a pulse form signal having significant light intensity (Em) appears as drawn in FIG. 2B. Thus, by detecting, one by one, each pulse form signal (significant light intensity) appearing as illustrated in FIG. 2B during the execution of the moving of the position of the light detection region CV and the light detection as described above, the light-emitting particles are detected individually, and by counting the number thereof, the information about the number, concentration or number density of the light-emitting particles existing in the measured region can be acquired. In the principle of the scanning molecule counting method, no statistical calculation processes, such as the calculation of the fluorescence intensity fluctuation, are conducted and the light-emitting particles are one by one detected, and therefore, the information about the concentration or number density of the particle is acquirable even in a sample solution with a low particle concentration at the level where no sufficiently accurate analysis is available in FCS, FIDA, etc.

2. The Principle of Identification of Light-Emitting Particle According to the Invention In the actual experiment system where the above-mentioned scanning molecule counting method is performed, the intensity of the excitation light in the light detection region is not uniform, and it usually decreases from the peak at the center of the light detection region to the edge of the region, and also, with respect to the path from the light detection region through a pinhole to a photodetector, the light intensity from the whole region of the light detection region does not absolutely uniformly reach the photodetector. Namely, the intensity of the light emitted by a certain light-emitting particle (or the light detected with a photodetector) changes depending upon the position of the light-emitting particle in the light detection region (and therefore, in the scanning molecule counting method, typically, when the intensity of a detected pulse form signal is within a definite limit assumed as light from a light-emitting particle, the signal is judged as a signal of the light from a light-emitting particle.). Thus, for example, in a case that light-emitting particles of two kinds are observed, even if the quantum yields or light-emitting ability (the intensity of light emitted on the same condition) of those light-emitting particles are mutually different, it is difficult to distinguish them with reference to the absolute values of their light intensities.

However, as already noted, in a case that a light-emitting particle has at least two light-emitting sites, since it is considered that the positions of these light-emitting sites in the light detection region are almost coincident when the size of the light-emitting particle is small enough compared with the light detection region, the ratio of the light intensities of these light-emitting sites does not depend on the position of the light-emitting particle in the light detection region of a microscope. For example, as schematically drawn in FIG. 3A, between when a light-emitting particle having a light-emitting site α which emits the light of the wavelength I and the light-emitting site β which emits the light of the wavelength II passes the approximate center of a light detection region (t1) and when the same light-emitting particle passes through the neighborhood of the margin of the light detection region (t2), the detected light intensities which are emitted from the respective light-emitting sites differ mutually as schematically drawn in FIG. 3B, while the ratios of the light intensity of the wavelength I to the light intensity of the wavelength II are considered to be substantially equal to each other. And, with reference to the ratio of the light intensities, it becomes possible to identify the light-emitting particle and to discriminate the kinds of light-emitting particle. Accordingly, in the present invention, by attaching two light-emitting sites having different emission wavelengths to a light-emitting particle to be observed or by utilizing light-emitting sites that a light-emitting particle intrinsically possesses, and referring to the ratio of the intensities of lights emitted from the light-emitting sites on the light-emitting particle, the identification of the light-emitting particle will be conducted.

According to the above-mentioned manner that a light-emitting particle is identified with reference to the ratio of the light intensities of at least two light-emitting sites on the light-emitting particle, it becomes possible to discriminate mutually different light-emitting particles in various manners. For example, as schematically drawn in FIG. 3C, in the presence of a light-emitting particle a having a light-emitting site α which emits light of wavelength I and a light-emitting site β which emits light of wavelength II and a light-emitting particle b having the light-emitting site α which emits the light of the wavelength I and two of the light-emitting sites β which emit the light of the wavelengths II (namely, when the number of one of light-emitting sites of one of light-emitting particles differs from the number of the corresponding light-emitting sites of the other of light-emitting particles), even if the light-emitting particle a crosses the approximate center of the light detection region (t1) while the light-emitting particle b crosses the neighborhood of the margin of the light detection region (t2), and thereby their light intensities of the wavelength II are almost equal to each other, the ratios of the light intensity of the wavelength I to the light intensity of the wavelength II differ mutually between the light-emitting particle a and the light-emitting particle b, and therefore, it can be judged which signal each of the signals is among the signals of the light-emitting particle a and the light-emitting particles b with reference to the light intensity ratio. And, by counting separately the numbers of the signals of the light-emitting particles a and b, it becomes possible to acquire information on the respective number density or concentration and the other information. In addition, in an alternative manner, for example, as schematically drawn in FIG. 3E, in the presence of a light-emitting particle a having a light-emitting site α which emits light of wavelength I and a light-emitting site β which emits light of wavelength II and a light-emitting particle c having the light-emitting site α which emits the light of the wavelength I and a light-emitting site γ which emits the light of the wavelengths II with a quantum yield different than the light-emitting site β (namely, when the kind of one of light-emitting sites of one of light-emitting particles differs from the kind of the corresponding light-emitting sites of the other of light-emitting particles), the light intensity ratios of the light-emitting sites will differ mutually between the light-emitting particles irrespective of where the light-emitting particles cross in the light detection region. Accordingly, it can be judged which signal each of the signals is among the signals of the light-emitting particle a and the light-emitting particles c, and it becomes possible to refer to those discriminatively. And, by counting separately the numbers of the signals of the light-emitting particles a and c, it becomes possible to acquire information on the respective number density or concentration and the other information.

The above-mentioned identifying or distinguishing method of light-emitting particle(s) is usable, for example, in testing whether or not certain two particles have combined with each other (Detection of binding and dissociating reaction) or in estimating the molecular size of a molecule whose number of light-emitting sites varies with its molecular size (see Embodiments 1 and 2 in the following.).

In this regard, in a case that the above-mentioned inventive method is used for discrimination of two or more kinds of light-emitting particle, it is advantageous in computing and comparing the light intensity ratios that at least a part of, preferably, all of light-emitting particles to be observation objects possess an identical light-emitting site. Thus, preferably, a common light-emitting site may be attached to all light-emitting particles to be observation objects. And each light-emitting particle is provided with a peculiar light-emitting site (specific light-emitting site) for identifying each light-emitting particle or discriminating each light-emitting particle from other light-emitting particles, and thereby, with the ratio of the light intensity from the specific light-emitting site and the light intensity from the common light-emitting site, each light-emitting particle may be characterized, identified or discriminated from other particles. Further, although the case where a single light-emitting particle has two kinds of light-emitting site thereon is explained in the example of the drawings, a single light-emitting particle may have three or more kinds of light-emitting site and the light-emitting particle may be characterized and identified with the ratio of light intensities from these light-emitting sites, and it should be understood that such a case belongs to the scope of the present invention also.

Operation Processes of Scanning Molecule Counting Method

In the embodiment of the scanning molecule counting method in accordance with the present invention with the optical analysis device 1 as illustrated in FIG. 1A, concretely, there are conducted (1) a process of preparation of a sample solution containing light-emitting particles, (2) a process of measuring the light intensity of a sample solution and (3) a process of analyzing the measured light intensity. FIG. 4 shows the operation processes in this embodiment in the form of a flow chart.

(1) Preparation of a Sample Solution

The particle to be observed in the inventive method may be an arbitrary particle as long as it is dispersed in a sample solution and moving at random in the solution, such as a dissolved molecule, and the particle may be, for instance, a biological molecule, i.e. a protein, a peptide, a nucleic acid, a lipid, a sugar chain, an amino acid, etc. or an aggregate thereof, a virus, a cell, a metallic colloid or other non-biological particle (Typically, the sample solution is an aqueous solution, but not limited to this, and it may be an organic solvent or other arbitrary liquids.). Also, the particle to be observed may be a particle which emits light by itself, or may be a particle to which a light emitting label (a fluorescent molecule, a phosphorescent molecule, and a chemiluminescent or bioluminescent molecule) is attached in an arbitrary manner.

Further, in order to perform the inventive method, each particle to be an observation object need to have the first and second light-emitting sites or the common light-emitting site and specific light-emitting site. Especially, as noted above, if each particle to be an observation object is provided with the common light-emitting site, it is advantageous in comparing or identifying detected particles, and therefore, an arbitrary light emitting label, e.g., a fluorescent dye may be attached to each particle to be an observation object as the common light-emitting site by an arbitrary way. In addition, for the characterization to identify and discriminate each particle to be an observation object, an arbitrary light emitting label, e.g. a fluorescent dye, may be attached to each particle as the specific light-emitting site by an arbitrary way. In this respect, when a particle to be an observation object has a light-emitting site intrinsically, this light-emitting site may be used as the common light-emitting site or specific light-emitting site. What is important is that a light-emitting particle to be an observation object has at least two light-emitting sites having different emission wavelengths so that the light intensity ratio can be computed out with the light intensities of the respective wavelengths detected in the light measurement explained later. How to select a particle to be an observed object in a sample solution, how to attach light emitting label(s) to a particles to be an observation object or how to select detected wavelengths may be appropriately determined by the performer of an experiment, and it should be understood that one skilled in the art can select various combinations of particles to be observed or light emitting labels and detected wavelength bands to realize the inventive method, and any cases belong to the scope of the present invention as long as the identification of a light-emitting particle is performed according to the present invention.

(2) Measurement of the Light Intensity of a Sample Solution

In the process of the measurement of the light intensity in the optical analysis in accordance with the scanning molecule counting method of this embodiment, there is performed measuring the light intensities in two or more wavelength bands, namely, in the emission wavelengths of the first and second light-emitting site (or the common light-emitting site and specific light-emitting site) individually and simultaneously, with driving the mirror deflector 17 to move the position of the light detection region within the sample solution (to scan in the sample solution) (FIG. 4—step 100). In the operation process, typically, after dispensing a sample solution into the well(s) 10 of the micro plate 9 and putting it on the stage of the microscope, when a user inputs to the computer 18 a command of a measurement start, the computer 18 executes programs (the process of changing the optical path in order to move the position of the light detection region in the sample solution, and the process of detecting light from the light detection region during the moving of the position of the light detection region) memorized in a storage device (not shown), and then illuminating the light detection region in the sample solution with the excitation light and measuring light intensity will be started. When the measurement was started, under the control of the operation process of the computer 18 according to the programs, from the light source 2, the light of the excitation wavelength of a light-emitting particle in the sample solution is emitted. Especially in this embodiment, since the lights of two or more wavelength bands are detected, the wavelength(s) of the excitation light(s) emitted from the light source 2 is (are) selected so that the lights of two or more wavelength bands to be detected will be emitted from the light-emitting particle(s). In this regard, when the excitation light wavelengths of the respective light-emitting sites on a light-emitting particle differ mutually, the laser light of two or more wavelength bands will be emitted simultaneously. On the other hand, the mirror deflector 17 drives the mirror 7 (galvanomirror) to move the position of the light detection region in the well 10 under the control of the operation process of the computer 18 according to the programs, and simultaneously with this, the photodetector 16 sequentially converts the detected light into an electric signal and transmits it to the computer 18, which generates the time series light intensity data from the transmitted signals and store it in an arbitrary manner. Especially, in this embodiment, the respective two or more photodetectors 16 detect the lights of mutually different wavelength bands, and thereby time series light intensity data is generated for each of the detected mutually different wavelength bands. Also, the photodetector 16 is typically a super high sensitive photodetector which can detect an arrival of a single photon, and thus the detection of light may be the photon counting performed in the manner of measuring sequentially the number of photons which arrive at the photodetector for every predetermined unit time (BIN TIME), for example, every 10 μs, during a predetermined time, and accordingly the time series light intensity data will be a time series photon count data.

The moving speed of the position of the light detection region during the measurement of the light intensity may be a predetermined velocity set arbitrarily, for example, experimentally or in order to meet the purpose of an analysis. In a case of acquiring the information on the number density or concentration based on the number of detected light emitting particles, the region size or volume through which the light detection region has passed is required, and therefore, preferably, the moving of the position of the light detection region is performed in a manner enabling the grasping of the moving distance. In this regard, because the interpretation of a measurement result will become easy if the elapsed time is proportional to the moving distance of the position of the light detection region, basically, it is preferable that the moving speed is constant, although not limited thereto.

By the way, regarding the moving speed of the position of the light detection region, in order to perform quantitatively precisely individual detection of a light-emitting particle to be observed from the measured time series light intensity data or the counting of the number of the light-emitting particles, it is preferable that the moving speed is set to a value quicker than the moving speed in the random motion, i.e., Brownian motion of a light-emitting particle. Since the light-emitting particle to be the observation object in this embodiment is a particle dispersed or dissolved in a solution and moving at random freely, its position moves with time owing to the Brownian motion. Thus, when the moving speed of the position of the light detection region is slower than the movement of a particle owing to the Brownian motion, the particle moves at random in the region as schematically drawn in FIG. 5A, whereby the light intensity changes at random (the excitation light intensity in the light detection region is reduced from the peak at the center of the region toward its outside.), so that it becomes difficult to determine a significant light intensity change corresponding to each light-emitting particle (a signal indicating light from a light-emitting particle). Then, preferably, as drawn in FIG. 5B, the moving speed of the position of the light detection region is set to be quicker than the average moving speed of a particle by the Brownian motion (diffusional moving velocity) so that the particle will cross the light detection region in an approximately straight line and thereby the profile of the change of the light intensity corresponding to each particle becomes almost uniform in the time series light intensity data as illustrated in the upper row of FIG. 5C (When a light-emitting particle passes through the light detection region in an approximately straight line, the profile of the light intensity change is similar to the excitation light intensity distribution.) and the correspondence between each light-emitting particle and light intensity can be easily determined.

Concretely, the time $\Delta t$ required for a light-emitting particle having a diffusion coefficient D to pass through the light detection region of radius $W_o$ (confocal volume) by Brownian motion is given from the expression of the relation of mean-square displacement:

$$(2W_o)^2 = 6D \cdot \Delta t \qquad (1)$$

as:

$$\Delta t = (2W_o)^2/6D \qquad (2),$$

and thus, the velocity of the light-emitting particle moving by Brownian motion (diffusional moving velocity) Vdif, becomes approximately $$V\text{dif} = 2W_o/\Delta t = 3D/W_o \qquad (3)$$

Then, with reference to this, the moving speed of the position of the light detection region may be set to a value sufficiently quicker than Vdif. For example, when the diffusion coefficient of a light-emitting particle is expected to be about $D=2.0\times10^{-10}$ m$^2$/s, Vdif will be $1.0\times10^{-3}$ m/s, supposing Wo is about 0.62 μm, and therefore, the moving speed of the position of the light detection region may be set to its 10 times or more, e.g. 15 mm/s, etc. In this regard, when the diffusion coefficient of a light-emitting particle is unknown, an appropriate moving speed of the position of the light detection region may be determined by repeating the executions of a preliminary experiment with setting various moving speeds of the position of the light detection region in order to find the condition that the profile of a light intensity variation becomes an expected profile (typically, similar to the excitation light intensity distribution).

(3) Analysis of Light Intensity

When the time series light intensity data of the respective light-emitting sites of a light-emitting particle in a sample solution are obtained by the above-mentioned processes, (i) Detection of a signal corresponding to light from a light-emitting particle on each light intensity data; (ii) Detection of signals simultaneously generated on the time series light intensity data of the respective light-emitting sites (simultaneous generation pulse) in the detected signals; (iii) Computation of the intensity ratio in simultaneous generation pulses; and (iv) Various analyses, such as calculation of a concentration of the light-emitting particle, may be performed sequentially in the computer 18 through processes in accordance with programs memorized in a storage device.

(i) Detection of a Signal Corresponding to a Light-Emitting Particle

When the track of one light-emitting particle in its passing through the light detection region is approximately straight as shown in FIG. 5B, the light intensity variation in the signal corresponding to the particle to be observed in the time series light intensity data has a bell shaped profile reflecting the light intensity distribution in the light detection region (determined by the optical system). Thus, when the time width $\Delta\tau$ for which the light intensity exceeding an appropriately set threshold value continues is in a predetermined range, the signal having the profile of the light intensity may be judged to correspond to one particle having passed through the light detection region, and thereby one light-emitting particle is detected. Further, when the light intensity distribution in the light detection region can be assumed as Gaussian distribution:

$$I = A \cdot \exp(-2t^2/a^2) \qquad (4),$$

and when the intensity A and the width a, computed by fitting the expression (4) to the profile of a significant light intensity (a profile which can be clearly judged not to be a background), are within the respective predetermined ranges, the profile of the light intensity may be judged to correspond to one particle having passed through the light detection region, and thereby the detection of one light-emitting particle will be done (The profile with the intensity A and the width a out of the predetermined ranges may be ignored as a noise or a contaminant in the analysis.).

As an example of operational methods of conducting a collective detection and the counting of light-emitting particles from time series light intensity, a smoothing treatment is performed to the time series light signal data (FIG. 5C, the upper row "detected result (unsettled)") (FIG. 4—step 110. FIG. 5C mid-upper row "smoothing"). Although the light emitted by a light-emitting particle is stochastic so that gaps will be generated in data values in minute time, such gaps in the data value can be disregarded by the smoothing treatment. The smoothing treatment may be done, for example, by the moving average method (for example, Adjacent average method and Savinsky-Golay method algorithm), Percentile filter method or FFT filter method. In this regard, parameters in performing the smoothing treatment, e.g., the number of datum points in one time of the averaging, the number of times of a moving average, etc. in the moving averages method, may be appropriately set in accordance with the moving speed (scanning speed) of the position of the light detection region and/or BIN TIME in the light intensity data acquisition.

Next, on the time series light intensity data after the smoothing treatment, in order to detect a time domain (pulse existing region) in which a significant pulse form signal (referred to as "pulse signal" hereafter) exists, the first differentiation value with time of the time series light intensity data after the smoothing treatment is computed (step 120). As illustrated in FIG. 5C, the mid-low row "time differential", in the time differential value of time series light signal data, the variation of the value increases at the time of the signal value change, and thereby, the start point and the end point of a significant signal can be determined advantageously by referring to the time differential value.

After that, a significant pulse signal is detected sequentially on the time series light intensity data, and it is judged whether or not the detected pulse signal is a signal corresponding to a light-emitting particle. Concretely, first, on the time series time-differential value data of the time series light intensity data, the start point and the end point of one pulse signal are searched and determined by referring to the time differential value sequentially, so that a pulse existing region will be specified (step 130). When one pulse existing region has been specified, the fitting of a bell-shaped function is applied to the smoothed time series light intensity data in the pulse existing region (FIG. 5C, the lower row "bell-shaped function fitting"), and then, parameters of the pulse of the bell-shaped function, such as the peak intensity (the maximum), Imax; the pulse width (full width at half maximum), w; the correlation coefficient in the fitting (of the least square method). etc. are computed (step 140). In this regard, although the bell-shaped function to be used in the fitting is typically Gauss type function, it may be Lorentz type function. And it is judged whether or not the computed parameters of the bell-shaped function are within the respective ranges assumed for the parameters of the bell-shaped profile drawn by a pulse signal detected when one light-emitting particle passes a light detection region, i.e., whether or not each of the peak intensity, the pulse width and the correlation coefficient of the pulse is within the corresponding predetermined range (step 150). Then, the signal, whose computed parameters of the bell-shaped function are judged to be within the ranges assumed in a light signal corresponding to one light-emitting particle, as shown in FIG. 6A left, is judged as a signal corresponding to one light-emitting particle, and thereby, one light-emitting particle will be detected. On the other hand, a pulse signal, whose computed parameters of the bell-shaped function are not within the assumed ranges, as shown in FIG. 6A right, is disregarded as noise.

The search and the judgment of a pulse signal in the processes of the above-mentioned steps 130-150 are repetitively carried out in the whole region of the time series light signal data (Step 160). Especially in this embodiment, the above-mentioned steps 110-160 may be performed in each of the time series light intensity data of the mutually different wavelength bands, and a pulse signal corresponding to a light-emitting particle may be detected in each of the wavelength bands. In this regard, although not illustrated, the number of the detected pulse signals may be counted during the search of pulse signals in the whole region of time series light intensity data. Also, the process of detecting individually signals of light-emitting particles from time series light intensity data may be conducted by an arbitrary way other than the above-mentioned way.

(ii) Detection of Simultaneously Generated Signals

When the detection of signals corresponding to light-emitting particles (pulse signals) in the time series light intensity data of two or more wavelength bands (namely, the time series light intensity data of the respective light-emitting sites) is completed as noted above, signals simultaneously generated on the time series light intensity data of two or more wavelength bands are detected among the detected signals (step 170). Concretely, for example, as illustrated in FIG. 6B, this detection may be conducted in a manner that, when the difference ΔT between time tp1 of the peak (maximum) of a pulse signal corresponding to a light-emitting particle in the time series light intensity data of one wavelength band (wavelength I) and time tp2 of the peak (maximum) of a pulse signal corresponding to a light-emitting particle in the time series light intensity data of the other wavelength band (wavelength II) is less than a predetermined value, it is judged that simultaneously generated pulse signals have been generated in the wavelength I and wavelength II. And, by repeating this judgment sequentially on time series light intensity data, all pulse signals simultaneously generated in the time series light intensity data of two or more wavelength bands (simultaneously generated pulse signals) are detected. Also, in an alternative manner of detection of simultaneously generated pulse signals, when the generation period (the start point-end point) of a signal on one of time series light intensity data and the generation period (the start point-end point) of a signal on the other of the time series light intensity data overlap, it may be judged that simultaneously generated pulse signals have been generated.

In this regard, in the inventive method, basically, a light-emitting particle to be an observation object carries at least two light-emitting sites having mutually different emission wavelengths, and therefore, theoretically, all pulse signals should become simultaneous generation pulses. However, in an actual experimental system, since it is difficult to spatially coincide CVs of the excitation lights of mutually different wavelengths due to chromatic aberration, etc., a region where only excitation light of one wavelength is illuminated may be produced in the light detection region, and in that case, a pulse signal is generated only on the time series light intensity data of one wavelength band. Therefore, the individual detection of simultaneous generation pulses is conducted as described above.

(iii) Computation of the Intensity Ratio in Simultaneous Generation Pulses

When simultaneous generation pulses are detected as noted above, the ratio of the intensity of the pulse signal in one of the wavelength bands and the intensity of the pulse signal in the other of the wavelength band (the ratio of the intensity of the pulse signal of the emission wavelength of the first light-emitting site and the intensity of the pulse signal of the second light-emitting site, or the ratio of the intensity of the pulse signal of the emission wavelength of the common light-emitting site and the intensity of the pulse signal of the specific light-emitting site) is computed for the respective simultaneous generation pulses. This ratio may be, e.g., a ratio of the intensities at the peaks of the respective pulse signals or a ratio of the integrated values of the intensities of the respective pulse signals. For example, in a case that the common light-emitting site and the specific light-emitting site are specified in a light-emitting particle to be an observation object, with the peak intensity Imax1 of a signal of the emission wavelength band of the common light-emitting site and the peak intensity Imax2 of a signal of the emission wavelength band of the specific light-emitting site, the intensity ratio may be given by:

$$Imax2/Imax1 \quad (5).$$

(iv) Analysis and Calculation of Concentration, Etc. (Step 180)

As already noted, since the above-mentioned ratio of signal intensities (light intensities) is considered to be a peculiar value of a light-emitting particle irrespective of the passing route of the light-emitting particle in the light detection region, the light-emitting particle is characterized with this ratio of signal intensities, and its identification, namely, the confirmation that the light-emitting particle is a assumed light-emitting particle or the discrimination of its kind, will be made. And, with the ratio of signal intensities or the identified result, each signal may be classified or the number of the signals may be counted by the classified signal.

For instance, in an experiment for testing a binding reaction of two particles, in a case that a common light-emitting site and a specific light-emitting site are given to a first particle and the specific light-emitting site is given to a second particle, if both the particles bind together, the intensity ratio of signals corresponding to a combination of both the particles becomes a double of the intensity ratio of signals corresponding to the first particle in simultaneously generated pulse signals, and therefore, through the comparison of the intensity ratios, it becomes possible to distinguish the signals corresponding to the combination and the signals corresponding to the first particle, and thereby, whether or not the binding reaction has occurred between the two particles can be confirmed. And by comparing the number of the signals corresponding to the combinations with the number of the signals corresponding to the first particle, it is also possible to evaluate the strength of the binding reaction. Moreover, as an alternative manner, in a molecule, etc. which can have various sizes, such as a nucleic acid, a polymerizing protein or an agglutinative protein, etc., when a molecule is prepared so that the number of specific light-emitting sites will increase in accordance with the molecular size, the intensity ratio of signals varies with the molecular size in simultaneously generated pulse signals, and therefore, with reference to the intensity ratio of signals, the estimation of molecular size and/or evaluation of the degree or strength of polymerization or aggregation become possible.

By the way, the number density or concentration of a light-emitting particle in time series light intensity data can be determined using the count value of the signals corresponding to the respective light-emitting particles (the number of signals) and the volume of the whole region which the light detection region has passed through during the acquisition of the time series light intensity data. However, the effective volume of the light detection region varies depending on the wavelength of excitation light or detected light, the numerical aperture of lenses and the adjustment condition of the optical system, and therefore, it is generally difficult to compute the effective volume of the light detection region from the design parameter values, and it is not easy to compute the whole volume which the light detection region has passed through, either. Further, as already noted, when excitation lights of two or more wavelength bands are simultaneously illuminated, since it is difficult to make the focal areas of the respective excitation lights mutually coincide completely due to chromatic aberration, etc., it is more difficult to compute the effective volume of the overlapped region of the focal regions of the respective excitation lights where simultaneous generation pulses are generated. Thus, typically, the light intensity measurement, the detection of particles and the counting thereof are performed as explained above with a solution having a known light-emitting particle concentration (reference solution) under the same condition as that for the measurement of a sample solution to be tested, and then, from the detected number of light-emitting particles and the concentration of the light-emitting particle in the reference solution, the volume of the whole region which the light detection region has passed through, i.e., the relation between the detected number and the concentration of the light-emitting particle, may be determined. Preferably, the light-emitting particle of a reference solution may be a light emitting label (fluorescent dye etc.) having the same wavelength characteristic as the corresponding light-emitting particle. Concretely, for example, supposing the detected number of the light-emitting particles is N in a reference solution of the particle concentration (number density) C, the volume Vt of the whole region which the light detection region has passed through is given by:

$$Vt=N/C \quad (6).$$

Alternatively, the plurality of solutions of different concentrations are prepared as reference solutions and the measurement is performed for each of the solutions, and then, the average value of the computed Vt is determined as the volume Vt of the whole region which the light detection region has passed through. Thus, when Vt is given, the concentration (number density) c of the light-emitting particle of the sample solution, whose counting result of the particles is n, is given by:

$$c=n/Vt \quad (7)$$

In this regard, the volume of the light detection region and the volume of the whole region which the light detection region has passed through may be given by an arbitrary method, for instance, using FCS and FIDA, instead of the above-mentioned method. Further, in the optical analysis device of this embodiment, there may be previously memorized in a storage apparatus of the computer 18 the information on the relations (expression (6)) between concentrations C and particle numbers N of various standard particles for assumed moving patterns of the light detection region, so that a user of the device can appropriately use the memorized information on the relation in conducting an optical analysis. In particular, in the present invention, since a light-emitting particle corresponding to simultaneously generated pulse signals is observed, a solution of known concentrations of light-emitting particles having emission wavelengths in all the observed wavelength bands may be prepared as a reference solution, and the detection and counting of simultaneously generated signals are performed on time series light intensity data obtained by the measurement of the light intensity with the solution, and then, from the count value and concentration, the total volume Vt of the region through which the light detection region has passed may be determined.

Thus, according to the above-mentioned inventive method, the identification of a light-emitting particle becomes achievable by referring to the intensity ratio of the signals acquired by the light measurement of two or more wavelength bands in the scanning molecule counting method, and based on change of the intensity ratio of signals, the information on an interaction, a size change of particles in a sample solution, etc. will be acquired. In this connection, it should be understood that, according to the above-mentioned method, even with a small amount of a sample solutions similarly to FCS, FIDA, etc., diverse information can be acquired with respect to a light-emitting particle of a lower concentration (several pM level) than the level at which a good measurement is possible in FCS, FIDA, etc. (typically about 1 nM).

In order to verify the validity of the present invention explained above, the experiments described below were conducted. In this regard, it should be understood that the following embodiments illustrate the validity of the present invention only, not intended to limit the scope of the present invention.

Embodiment 1

Detection Experiment of Oligonucleotides Labeled with Two Differently Colored Fluorescent Dyes In accordance with the inventive method, it was verified that discrimination between a single strand oligonucleotide and a double strand oligonucleotide was possible.

For the samples, there were prepared a single strand oligonucleotide (1 T-A) of 31 bases having a base sequence of sequence No. 1 in which 5' end has been modified with a fluorescent dye Alexa647 and 3' end has been modified with a fluorescent dye TAMRA as schematically drawn on FIG. 7A left, and a double strand oligonucleotide (2 T-A)(an oligonucleotide formed by associating 1T-A with an oligonucleotide (1-A) modified with TAMRA at 5' end and having a base sequence of sequence No. 2, complementary to the sequence of 1T-A) as schematically drawn on FIG. 7A right. The 2T-A was prepared by mixing 1T-A and 1 A so as to be at 1 µM, respectively, in a buffer solution containing 10 mM Tris-HCl (pH 8.0), 5 mM EDTA and 100 mM NaCl; placing the mixed solution at 94° C. in 5 minutes so that thermal denaturation would be caused; and subsequently lowering the temperature to room temperature to conduct an annealing treatment. Then, as the sample solutions, there were prepared separately solutions containing 1T-A and 2T-A at about 2 nM(s), respectively, in the above-mentioned buffer solution. In this connection, Alexa647, when excited with 633-nm excitation light, emits fluorescence of about 650-705-nm. On the other hand, TAMRA, when excited with 543-nm excitation light, emits fluorescence of about 550-620-nm. (In this embodiment. Alexa647 is to be the common light-emitting site, and TAMRA is to be the specific light-emitting site.)

In the light measurement and analysis, a single molecule fluorescence measuring apparatus MF-20 (Olympus Corporation), equipped with the optical system of a confocal fluorescence microscope and a photon counting system, was used as the optical analysis device, and time series light intensity data (photon count data) were acquired for the above-mentioned respective sample solutions in accordance with the manner explained in the above-mentioned "(2) Measurement of the light intensity of a sample solution". In that time, a 543 nm laser light and a 633-nm laser light were used for excitation lights, and, using band pass filters, the lights of two wavelength bands, 566 to 590 nm and 660 to 710 nm, were simultaneously and separately measured for the excitation lights of 543 nm and 633 nm, respectively, and the time series light intensity data were generated for each of the excitation light of 543 nm and excitation light of 633 nm. The moving speed of the position of the light detection region in the sample solution was set to 15 mm/second; BIN TIME was set to 10 µsec.; and for the respective sample solutions, the measurement for 2 seconds was performed, respectively. After the light intensity measurement, in accordance with the procedures described in the above-mentioned "(3) (i) Detection of a signal corresponding to a light-emitting particle", the smoothing treatment was applied to the time series light intensity data of each wavelength band acquired with each sample solution, and after determining the start points and the end points of pulse signals in the smoothed data, the fitting of a Gauss function to each pulse signal was carried out by the least square method, and a peak intensity, a pulse width (full width at half maximum) and a correlation coefficient (in the Gauss function) were determined. Then, only the pulse signal satisfying the following conditions:

20 µsec.<pulse width<400 µsec.

Peak intensity>1(photon/10 µsec.)

Correlation coefficient>0.95    (A)

was judged as a signal corresponding to a light-emitting particle (1T-A, 2T-A), while a pulse signal which did not satisfy the above-mentioned conditions was disregarded as noise.

Next, through comparing the pulse signals judged as a light-emitting particle on the data of the excitation light of 543 nm and the data of the excitation light of 633 nm, when the difference in the time of the peak (maximum) between pulse signals was within 30 µseconds, those pulse signals were judged and extracted as a simultaneously generated pulse signal (a simultaneous generation pulse signal), and for the respective signals, the ratios (Imax2/Imax1) of the peak intensity Imax2 of the signal on the data of the excitation light of 543 nm and the peak intensity Imax1 of the signal on the data of the excitation light of 633 nm were computed.

FIG. 7B shows the numbers of generations of simultaneous generation pulses against the peak intensity ratio with respect to the simultaneous generation pulses obtained in the above-mentioned processes. As understood from the drawing, the distribution (white bar) of 1T-A and the distribution (black bar) of 2T-A forms bell shape, respectively, and the average of the peak intensity ratios Imax2/Imax of 1T-A was 0.73 (SD=0.22) while the average of the peak intensity ratios Imax2/Imax1 of 2 T-A was 1.52 (SD=0.50). That is, the peak intensity ratio of 2T-A is about twice the peak intensity ratio of 1T-A, and the distributions of the peak intensity ratios were quantized in general in accordance with the number of TAMRA(s) (specific light-emitting site) on the light-emitting particle. In this result, signals whose peak intensity ratio was about 0.8 or less can be identified to correspond to 1T-A, and signals whose peak intensity ratio was about 1.5 or more can be identified to correspond to 2T-A. Moreover, the above-mentioned result also shows that 1T-A and 1-A were associated with each other to form 2T-A.

Thus, according to the present embodiment, It was shown that the identification of a light-emitting particle, especially the discrimination of a kind of light-emitting particle is possible by selecting appropriately the number of specific light-emitting sites according to a kind of light-emitting particle and referring to the ratios of the light intensity of the specific light-emitting site and the light intensity of the common light-emitting site in the respective simultaneously generated pulse signals in accordance with the inventive method.

Embodiment 2

Detection Experiment of Size of a Nucleic Acid Molecule Labeled with Two Differently Colored Fluorescent Dyes It was verified that nucleic acid molecules having various chain lengths were discriminable by the inventive method.

For the samples, there were prepared DNAs, modified at 5' end with a fluorescent dye ATTO647N having a base sequence of sequence No. 3 with the chain length of 100 bp; a base sequence of sequence No. 4 with the chain length of 200 bp; a base sequence of sequence No. 5 with the chain length of 400 bp; a base sequence of sequence No. 6 with the chain length of 800 bp; and a base sequence of sequence No. 7 with the chain length of 1.5 kbp, respectively (called A100 bp, A200 bp, A400 bp, A800 bp, and A1.5 kbp, respectively, in the following.). In the preparation of these DNA, first, each of the above-mentioned DNAs was produced by PCR using a plasmid pUC19 as a mold; an oligonucleotide having a base sequence of sequence No. 8 and modified ATTO647N at 5' end as a common primer; non-labeled oligonucleotides each having a base sequence of sequence No. 9-13 as a primer for DNA of the corresponding chain length A100 bp, A200 bp, A400 bp, A800 bp and A1.5 kbp, respectively; and AmpliTaq Gold (Registered trademark). Subsequently, unreacted primers were removed from the PCR product using Wizard SV Gel and PCR Clean-Up System (Promega), and according to electrophoresis using a bio-analyzer (Agilent), the presences or absences and concentrations of DNAs of the above-mentioned chain lengths were checked. For the sample solutions, after the DNAs of the respective chain lengths were dissolved so as to be at 10 nM in a buffer solution (10 mM Tris-HCl (pH 8.0), 5 mM EDTA, 100 mM NaCl), the solutions were prepared by diluting the DNAs so that DNA concentration would be at 1 pM, 10 pM, 100 pM and 1 nM in the presence of a fluorescent dye SYTOX Orange at 10 nM (Invitrogen) and putting them at rest at room temperature for 30 minutes or more. In this connection, ATTO647N, when excited with the 633-nm excitation light, emits fluorescence in about 665-700-nm, and SYTOX Orange (in the following, SYTOX O.), when excited with 543-nm excitation light, emits fluorescence in about 550-630-nm. Especially, SYTOX O. is an intercalator type fluorescent dye whose fluorescence intensity increases about 500 times when it enters into a base pair of DNA. Thus, as schematically drawn on FIG. 8A, when the chain length of DNA becomes long, the bonding number of SYTOX O. per single DNA molecule will increase, and accordingly, the increase of the amount of light emission per molecule (per unit excitation light amount) is expected. (In this embodiment, ATTO647N is to be the common light-emitting site, and SYTOX O. is to be the specific light-emitting site.)

Measurement and analysis of lights were conducted similarly to Embodiment 1 for the above-mentioned respective sample solutions, in which simultaneous generation pulses were detected, and for the detected simultaneous generation pulses, the ratios (Imax2/Imax1) of peak intensity Imax2 of a signal of SYTOX O. (a signal on the data of the excitation light of 543 nm) and peak intensity Imax1 of a signal of ATTO647N (a signal on the data of the excitation light of 633 nm) were computed.

The following table 1 shows the numbers of simultaneously generated pulses in the respective sample solutions containing DNAs of the respective chain lengths at the respective concentrations obtained in the above-mentioned processes.

TABLE 1

The Number of Detected Simultaneously Generated Pulses In Sample Solutions Containing DNAs Having Different Chain Lengths at Various Concentrations

|  | A100 bp | A200 bp | A400 bp | A800 bp | A1.5 kbp |
|---|---|---|---|---|---|
| 1 pM | 0 | 1 | 1 | 5 | 8 |
| 10 pM | 3 | 7 | 27 | 49 | 35 |
| 100 pM | 27 | 86 | 220 | 255 | 434 |
| 1 nM | 460 | 1530 | 2643 | 3830 | 3408 |

As shown in Table 1, the number of the simultaneous generation pulses increased with the DNA concentration in the solution for any of the sample solutions of DNAs of the respective chain lengths. This shows that the respective simultaneously generated pulses are signals corresponding to a DNA molecule. In this regard, the reason that the numbers of simultaneously generated pulses in the same concentrations differed depending upon the chain length is that, as the chain length becomes longer, the number of the intercalators binding to nucleic acid increases so that it can be easier to catch the pulses from the intercalators, and thereby the apparent number of the simultaneously generated pulses will increase.

FIG. 8B is a graph in which the averages of the peak intensity ratios Imax2/Imax1 of the above-mentioned respective simultaneously generated pulses for the respective chain lengths of DNAs are plotted against the chain length of DNA. As understood from the drawing, the peak intensity ratio was almost proportional to the chain length of DNA. This result indicates that the number of SYTOX O.s entering into base pairs of DNA increases with increase of the chain length of DNA, and thereby the ratio of the intensity of the signal of SYTOX to the intensity of the signal of ATTO647N (which is attached alone to each DNA molecule). That is, according to this result, it has been shown that, in accordance with the inventive method, by referring to the peak intensity ratio, the chain length of DNA or the size of one molecule can be checked and the discrimination of a light-emitting particle according to the chain length of DNA or the size of one molecule is possible.

Thus, as understood from the results of the above-mentioned embodiments, in accordance with the above-mentioned inventive method, in the scanning molecule counting method, by referring to the ratio of the light intensities of at least two light-emitting sites of a single light-emitting particle, the identification of the light-emitting particle becomes possible, and the discrimination of a kind of light-emitting particle, the detection of the size of a light-emitting particle, or the discrimination of light-emitting particles based on the size of light-emitting particle become possible. Furthermore, it has been shown that, according to the present invention, the identification of a light-emitting particle can be individually performed for a signal corresponding to a single light-emitting particle by the way of detecting light from a light-emitting particle individually and computing the light intensity ratio, and therefore, in a test of an interaction (a binding reaction or a decomposition reaction) of light-emitting particles, the detection of the presence or absence of the interaction of light-emitting particles and/or estimation of the degree of its strength are possible even in a case that the concentrations of light-emitting particles in a sample solution are significantly lower than the range usable in FIDA, or in a case that the interaction is weak so that combinations or decomposition products can be produced at only a relatively small amount with which their detection is difficult in FIDA.

The invention claimed is:

1. A method of detecting and analyzing light from a light-emitting particle dispersed and moving at random in a sample solution using an optical system of a confocal microscope or a multiphoton microscope, the method comprising steps of:
preparing the sample solution containing a light-emitting particle dispersed and moving at random in the sample solution, the light-emitting particle having a first light-emitting site and a second light-emitting site which has a different emission wavelength from that of the first light-emitting site;
moving a position of a light detection region of the optical system in the sample solution by changing an optical path of the optical system;
measuring individually and simultaneously light intensity of the first light-emitting site and light intensity of the second light-emitting site from the light detection region during the moving of the position of the light detection region in the sample solution;
generating a first light intensity data of the light intensity of the first light-emitting site and a second light intensity data of the light intensity of the second light-emitting site;
detecting individually in the first and the second light intensity data a signal indicating light of a single light-emitting particle based on a variation in time of the light intensity, the signal being detected when the variation in time of the light intensity has a bell shaped profile which is expected from the single light-emitting particle moving relatively inside the light detection region;
identifying the single light-emitting particle with a ratio of the light intensity of the first light-emitting site and the light intensity of the second light-emitting site in respective signals simultaneously generated on the first light intensity data and the second light intensity data.

2. The method of claim 1, wherein the first light-emitting site is a common light-emitting site which at least a part of light-emitting particles in the sample solution have in common, and the second light-emitting site is a specific light-emitting site characterizing the respective light-emitting particles.

3. The method of claim 1, wherein a kind of the single light-emitting particle is identified with the ratio of the light intensity of the first light-emitting site and the light intensity of the second light-emitting site.

4. The method of claim 1, wherein a size of the single light-emitting particle is determined with the ratio of the light intensity of the first light-emitting site and the light intensity of the second light-emitting site.

5. The method of claim 1, wherein a kind of the second light-emitting site differs depending upon a kind of light-emitting particle.

6. The method of claim 1, wherein a number of the second light-emitting sites differs depending upon a kind of light-emitting particle.

7. The method of claim 6, wherein the number of the second light-emitting sites which the single light-emitting particle possesses increases as a size of the light-emitting particle increases.

8. The method of claim 1, further comprising a step of counting a number of the identified single light-emitting particles.

9. The method of claim 1, moving the position of the light detection region at a velocity quicker than a diffusion moving velocity of the light-emitting particle in the sample solution.

10. The method of claim 8, further comprising a step of determining a number density or concentration of the light-emitting particle based on the number of the identified single light-emitting particles.

* * * * *

SEQUENCE LISTING

<160> NUMBER OF SEQ ID NOS: 13

<210> SEQ ID NO 1
<211> LENGTH: 31
<212> TYPE: DNA
<213> ORGANISM: Artificial
<220> FEATURE:
<223> OTHER INFORMATION: used for a test in a scanning molecule counting method

<400> SEQUENCE: 1
gagatgttgc ttctcttaat tccttgatag c				31

<210> SEQ ID NO 2
<211> LENGTH: 31
<212> TYPE: DNA
<213> ORGANISM: Artificial
<220> FEATURE:
<223> OTHER INFORMATION: used for a test in a scanning molecule method

<400> SEQUENCE: 2
gctatcaagg aattaagaga agcaacatct c				31

<210> SEQ ID NO 3
<211> LENGTH: 100
<212> TYPE: DNA
<213> ORGANISM: Artificial
<220> FEATURE:
<223> OTHER INFORMATION: used for a test in a scanning molecule counting method

<400> SEQUENCE: 3
gaaacagcta tgaccatgat tacgccaagc ttgcatgcct gcaggtcgac tctagaggat		60 ccccgggtac cgagctcgaa ttcactggcc gtcgttttac					100

<210> SEQ ID NO 4
<211> LENGTH: 200
<212> TYPE: DNA
<213> ORGANISM: Artificial
<220> FEATURE:
<223> OTHER INFORMATION: used for a test in a scanning molecule counting method

<400> SEQUENCE: 4
aatgtgagtt agctcactca ttaggcaccc caggctttac actttatgct tccggctcgt		60 atgttgtgtg gaattgtgag cggataacaa tttcacacag gaaacagcta tgaccatgat		120 tacgccaagc ttgcatgcct gcaggtcgac tctagaggat ccccgggtac cgagctcgaa		180 ttcactggcc gtcgttttac								200

<210> SEQ ID NO 5
<211> LENGTH: 400
<212> TYPE: DNA
<213> ORGANISM: Artificial
<220> FEATURE:
<223> OTHER INFORMATION: used for a test in a scanning molecule counting method

<400> SEQUENCE: 5
tggataaccg tattaccgcc tttgagtgag ctgataccgc tcgccgcagc cgaacgaccg		60 agcgcagcga gtcagtgagc gaggaagcgg aagagcgccc aatacgcaaa ccgcctctcc		120 ccgcgcgttg gccgattcat taatgcagct ggcacgacag gtttcccgac tggaaagcgg		180 gcagtgagcg caacgcaatt aatgtgagtt agctcactca ttaggcaccc caggctttac		240

```
actttatgct tccggctcgt atgttgtgtg gaattgtgag cggataacaa tttcacacag    300
gaaacagcta tgaccatgat tacgccaagc ttgcatgcct gcaggtcgac tctagaggat    360
ccccgggtac cgagctcgaa ttcactggcc gtcgttttac                          400
```

<210> SEQ ID NO 6
<211> LENGTH: 800
<212> TYPE: DNA
<213> ORGANISM: Artificial
<220> FEATURE:
<223> OTHER INFORMATION: used for a test in a scanning molecule counting
      method

<400> SEQUENCE: 6

```
tcaagacgat agttaccgga taaggcgcag cggtcgggct gaacgggggg ttcgtgcaca     60
cagcccagct tggagcgaac gacctacacc gaactgagat acctacagcg tgagctatga    120
gaaagcgcca cgcttcccga agggagaaag gcggacaggt atccggtaag cggcagggtc    180
ggaacaggag agcgcacgag ggagcttcca gggggaaacg cctggtatct ttatagtcct    240
gtcgggtttc gccacctctg acttgagcgt cgattttgt  gatgctcgtc aggggggcgg    300
agcctatgga aaaacgccag caacgcggcc ttttacggt  tcctggcctt ttgctggcct    360
tttgctcaca tgttctttcc tgcgttatcc cctgattctg tggataaccg tattaccgcc    420
tttgagtgag ctgataccgc tcgccgcagc cgaacgaccg agcgcagcga gtcagtgagc    480
gaggaagcgg aagagcgccc aatacgcaaa ccgcctctcc ccgcgcgttg gccgattcat    540
taatgcagct ggcacgacag gtttcccgac tggaaagcgg gcagtgagcg caacgcaatt    600
aatgtgagtt agctcactca ttaggcaccc caggctttac actttatgct tccggctcgt    660
atgttgtgtg gaattgtgag cggataacaa tttcacacag gaaacagcta tgaccatgat    720
tacgccaagc ttgcatgcct gcaggtcgac tctagaggat ccccgggtac cgagctcgaa    780
ttcactggcc gtcgttttac                                                800
```

<210> SEQ ID NO 7
<211> LENGTH: 1500
<212> TYPE: DNA
<213> ORGANISM: Artificial
<220> FEATURE:
<223> OTHER INFORMATION: used for a test in a scanning molecule method

<400> SEQUENCE: 7

```
acaattaata gactggatgg aggcggataa agttgcagga ccacttctgc gctcggccct     60
tccggctggc tggtttattg ctgataaatc tggagccggt gagcgtgggt ctcgcggtat    120
cattgcagca ctgggccag  atggtaagcc ctcccgtatc gtagttatct acacgacggg    180
gagtcaggca actatggatg aacgaaatag acagatcgct gagataggtg cctcactgat    240
taagcattgg taactgtcag accaagttta ctcatatata ctttagattg atttaaaact    300
tcatttttaa tttaaaagga tctaggtgaa gatcctttt  gataatctca tgaccaaaat    360
cccttaacgt gagttttcgt tccactgagc gtcagacccc gtagaaaaga tcaaaggatc    420
ttcttgagat ccttttttc  tgcgcgtaat ctgctgcttg caaacaaaaa aaccaccgct    480
accagcggtg gtttgtttgc cggatcaaga gctaccaact ctttttccga aggtaactgg    540
cttcagcaga gcgcagatac caaatactgt tcttctagtg tagccgtagt taggccacca    600
cttcaagaac tctgtagcac cgcctacata cctcgctctg ctaatcctgt taccagtggc    660
tgctgccagt ggcgataagt cgtgtcttac cgggttggac tcaagacgat agttaccgga    720
```

```
taaggcgcag cggtcgggct gaacgggggg ttcgtgcaca cagcccagct tggagcgaac      780
gacctacacc gaactgagat acctacagcg tgagctatga gaaagcgcca cgcttcccga      840
agggagaaag gcggacaggt atccggtaag cggcagggtc ggaacaggag agcgcacgag      900
ggagcttcca gggggaaacg cctggtatct ttatagtcct gtcgggtttc gccacctctg      960
acttgagcgt cgattttgt gatgctcgtc agggggcgg agcctatgga aaaacgccag      1020
caacgcggcc ttttacggt tcctggcctt tgctggcct tttgctcaca tgttctttcc      1080
tgcgttatcc cctgattctg tggataaccg tattaccgcc tttgagtgag ctgataccgc      1140
tcgccgcagc cgaacgaccg agcgcagcga gtcagtgagc gaggaagcgg aagagcgccc      1200
aatacgcaaa ccgcctctcc ccgcgcgttg gccgattcat taatgcagct ggcacgacag      1260
gtttcccgac tggaaagcgg gcagtgagcg caacgcaatt aatgtgagtt agctcactca      1320
ttaggcaccc caggctttac actttatgct tccggctcgt atgttgtgtg gaattgtgag      1380
cggataacaa tttcacacag gaaacagcta tgaccatgat tacgccaagc ttgcatgcct      1440
gcaggtcgac tctagaggat ccccgggtac cgagctcgaa ttcactggcc gtcgttttac      1500
```

<210> SEQ ID NO 8
<211> LENGTH: 18
<212> TYPE: DNA
<213> ORGANISM: Artificial
<220> FEATURE:
<223> OTHER INFORMATION: used for a common primer for producing DNA
      having various lengths

<400> SEQUENCE: 8
gtaaaacgac ggccagtg                                                    18

<210> SEQ ID NO 9
<211> LENGTH: 18
<212> TYPE: DNA
<213> ORGANISM: Artificial
<220> FEATURE:
<223> OTHER INFORMATION: used for a primer for produing 100 bp DNA

<400> SEQUENCE: 9
gaaacagcta tgaccatg                                                    18

<210> SEQ ID NO 10
<211> LENGTH: 18
<212> TYPE: DNA
<213> ORGANISM: Artificial
<220> FEATURE:
<223> OTHER INFORMATION: used for a primer for producing 200 bp DNA

<400> SEQUENCE: 10
aatgtgagtt agctcact                                                    18

<210> SEQ ID NO 11
<211> LENGTH: 18
<212> TYPE: DNA
<213> ORGANISM: Artificial
<220> FEATURE:
<223> OTHER INFORMATION: used for a primer for producing 400 bp DNA

<400> SEQUENCE: 11
tggataaccg tattaccg                                                    18

<210> SEQ ID NO 12
<211> LENGTH: 18

```
<212> TYPE: DNA
<213> ORGANISM: Artificial
<220> FEATURE:
<223> OTHER INFORMATION: used for a primer for producing 800 bp DNA

<400> SEQUENCE: 12
tcaagacgat agttaccg                                                  18

<210> SEQ ID NO 13
<211> LENGTH: 19
<212> TYPE: DNA
<213> ORGANISM: Artificial
<220> FEATURE:
<223> OTHER INFORMATION: used for a primer for producing 1.5k bp DNA

<400> SEQUENCE: 13
acaattaata gactggatg                                                 19
```